(12) United States Patent
Takenaka et al.

(10) Patent No.: US 8,409,850 B2
(45) Date of Patent: Apr. 2, 2013

(54) MICROORGANISM TESTING DEVICE

(75) Inventors: Kei Takenaka, Kashiwa (JP); Yasuhiko Sasaki, Tsuchiura (JP); Ryo Miyake, Tsukuba (JP)

(73) Assignee: Hitachi Engineering & Services Co., Ltd., Ibaraki (JP)

(*) Notice: Subject to any disclaimer, the term of this patent is extended or adjusted under 35 U.S.C. 154(b) by 1134 days.

(21) Appl. No.: 11/964,154

(22) Filed: Dec. 26, 2007

(65) Prior Publication Data

US 2008/0153153 A1    Jun. 26, 2008

(30) Foreign Application Priority Data

Dec. 26, 2006 (JP) .................................. 2006-348753

(51) Int. Cl.
*C12M 1/34* (2006.01)
*C12M 3/00* (2006.01)

(52) U.S. Cl. ............... 435/288.5; 435/287.2; 435/288.6; 435/288.7

(58) Field of Classification Search ............... 435/287.2, 435/288.5–288.7, 287.1–287.3, 287.5
See application file for complete search history.

(56) References Cited

U.S. PATENT DOCUMENTS

| | | | | |
|---|---|---|---|---|
| 5,637,469 A | * | 6/1997 | Wilding et al. | 435/7.21 |
| 6,143,247 A | * | 11/2000 | Sheppard et al. | 422/63 |
| 2006/0073584 A1 | * | 4/2006 | Sasaki et al. | 435/288.5 |

FOREIGN PATENT DOCUMENTS

| | | |
|---|---|---|
| JP | 64-53965 U | 4/1989 |
| JP | 2005-245317 | 9/2005 |
| JP | 2006-051459 | 2/2006 |
| JP | 2006-121934 | 5/2006 |
| WO | WO 2006/115663 A2 | 11/2006 |

OTHER PUBLICATIONS

C. Buhlmann, et al., "A New Tool for Routine Testing of Cellular Protein Expression: Integration of Cell Staining and Analysis of Protein Expression on a Microfluid Chip-Based System", Journal of Biomolecular Techniques, vol. 14, Issue 2, pp. 119-127, Jun. 2003.

* cited by examiner

*Primary Examiner* — Michael Marcheschi
*Assistant Examiner* — Shanta G Doe
(74) *Attorney, Agent, or Firm* — Antonelli, Terry, Stout & Kraus, LLP.

(57) ABSTRACT

A microorganism testing device includes a measurement chip having a specimen container; a reaction container for mixing a specimen and a dyeing reagent; a bacteria detection portion irradiated with excitation light; a detection liquid waste container a solution flow path which connects the specimen container, the reaction container and the bacteria detection portion, and ventilation ports which are connected to the specimen container, the reaction container and the detection liquid waste container, through a air flow path and is connected to a chip connecting tube. Bacteria are detected in the bacteria detection portion by switching of the states of the containers between a sealed state and a state open to the atmospheric pressure, by moving the specimen to the reaction container to mix and stir the specimen and the dyeing reagent, and by moving of the liquid mixture to the detection liquid waste container.

13 Claims, 15 Drawing Sheets

MICROORGANISM TESTING DEVICE

BACKGROUND OF THE INVENTION

1. Field of the Invention

The present invention relates to a microorganism testing device measuring microorganisms included in foods.

2. Description of the Related Art

Conventionally, there have been known measuring devices which execute various kinds of methods for quick and simple measurement of the number of viable bacteria. Especially, a device for measuring the number of bacteria has become of major interest as a technique for quick and direct measurement of the number of viable bacteria, wherein the device uses a fluorescence flow cytometry method.

The fluorescence flow cytometry method is a particle measuring method, in which the diameter of specimen flow including specimens dyed with a fluorochrome is made smaller, and the specimen is discharged in a flow one by one for measurement. A device for measuring the number of bacteria, which uses the above method, may measure a specimen one by one in a short time.

Moreover, in the fluorescence flow cytometry method, the diameter of the specimen flow is made narrow down by forming a laminar flow of a specimen and sheath liquid for making use of a pressure difference between those of two liquids in order to prevent elements in the specimen from adhering to the wall of the flow path.

Furthermore, in order to implement the method with a low cost, or to eliminate washing processing, there has been known a method in which a flow path portion used for measurement by the fluorescence flow cytometry method is made into a disposable chip, so that the flow path portion to be measured is disposed of without being re-used after measurement being made in the disposable chip. The method has been described in, for example, a Journal of Biomolecular Techniques, Vol. 14, Issue 2, pp. 119-127.

In the above-described technology, it has been required, when the number of viable bacteria included in foods is measured, to remove residual food from a specimen before a tester injects the specimen and sheath liquid into a well of the chip, because it has not been considered that measurement of bacteria is rapidly executed for various kinds of food specimens.

Moreover, the flow cytometry method has required large residual food included in a specimen to be removed in a complete manner because a specimen including bacteria is poured into a flow of the sheath liquid from a thin nozzle with a diameter of about 100 µm.

Moreover, both reaction between a specimen and a dyeing reagent as batch processing, and measurement by the fluorescence flow cytometry method as flow processing are required to be compatible with each other in a disposable chip. Accordingly, a container (hereinafter, called a reaction container) in the chip for reacting liquid mixture of the specimen and the dyeing reagent is required to have two conflicting functions. That is, one is a function by which, when reacting, a liquid mixture is prevented from flowing into a detection flow path from the reaction container, and the other is a function by which, when measuring, the whole quantity of the liquid mixture is securely delivered from the reaction container to the detection flow path.

Furthermore, small impurities also have a possibility to exert an unfavorable influence upon measurement results, for example, because the impurities produce auto-fluorescence. Accordingly, it is indispensable for the small impurities to be removed when the device is required to stably be operated.

For example, when a bacteria is measured using fluorescence, a material, such as a pigment and chlorophyll, having auto-fluorescence property, and a cell which, by a fluorescent reagent, emits fluorescence similar to that of a bacteria are considered as impurities with a difficulty in distinction from the fluorescence caused by the bacteria. As the pigment and the chlorophyll are much smaller than the bacteria (about 1 µm), and an animal cell and a plant cell are much larger than the bacteria, complex operations are required to extract only the bacteria. These operations are complex in the same manner as the dyeing operations to require a professional skill.

SUMMARY OF THE INVENTION

The object of the present invention is to solve the problems of the above-described technologies and to stably measure bacteria in foods by easy operations by carrying out pretreatment of residual food removal and dyeing bacteria, and quick measurement of the number of bacteria, in one disposable chip.

In order to solve the above-described problem, the present invention is a microorganism testing device comprising a measurement chip for holding a specimen including bacteria and a dyeing reagent in the chip, a holder for holding the measurement chip and controlling the temperature of the chip, and a delivery device for delivering the specimen and the dyeing reagent through a chip connecting tube connected to the measurement chip, which testing device irradiates a specimen in the measurement chip with excitation light to detect the bacteria as an electric signal, wherein the measurement chip includes: a specimen container for holding the specimen; a reaction container for mixing the specimen and a dyeing reagent for reaction into a liquid mixture; a bacteria detection portion being irradiated with the excitation light; a detection liquid waste container into which the liquid mixture which has passed the bacteria detection portion enters; a solution flow path which connects the specimen container, the reaction container and the bacteria detection portion, and in which the specimen and the liquid mixture flow; and a ventilation port which is connected to the specimen container, the reaction container and the detection liquid waste container, through a air flow path and is connected to the chip connecting tube, wherein bacteria are detected in the bacteria detection portion by applying pressure to the specimen container, the reaction container, and the detection liquid waste container from the delivery device through the ventilation port, by switching of the states of the specimen container, the reaction container and the detection liquid waste container between a sealed state and a state open to the atmospheric pressure, by moving the specimen to the reaction container to mix and stir the specimen and the dyeing reagent in the reaction container, and by moving of the liquid mixture to the detection liquid waste container through the bacteria detection portion.

According to present invention, the specimen container, the reaction container, and the detection liquid waste container are each switched between a sealed state and a state open to the atmospheric pressure through the ventilation port for movement of a specimen, and for mixing and stirring the specimen with a dyeing reagent. Thereby, removal of residual foods, dyeing of bacteria, and measurement of the number of acteria may be continuously performed in one chip.

Accordingly, work load of a tester, and a possibility that a tester is exposed to a dyeing reagent are reduced. Thereby, stable measurement results may be obtained, not depending on the skill of a tester. Moreover, required reagent costs may be reduced, because a surplus amount of used dyeing reagents may be decreased.

DESCRIPTION OF THE PREFERRED EMBODIMENTS

Recently, food poisoning caused by a microorganism such as enterohemorrhagic *Escherichia coli* O157 has become a big social problem, and demands for the safety of foods have become higher and higher among the general consumers. Sanitary control of foods has become an essential condition for the safety of provided foods among food suppliers from general eating houses to large companies having food manufacturing plants.

For a food sanitation manager, the number of viable bacteria, such as general viable bacteria and coliform bacteria, included in foods is assumed to be used as an objective index for a "sanitary" food. Conventionally, a culture method has been used as means for measuring the number of viable bacteria. According to the method, suspension liquid of a food specimen is applied on culture media, and a colony formed of growing microorganisms is measured. However, the culture method requires long inspection time, because it requires from one to several days for the microorganisms to form the colony. For the food suppliers, the culture method is not actually an inspection one to secure the safety of shipped foods, but a method which is only a cause investigation method after food poisoning is generated. Furthermore, human errors have been generated and the inspection cost has become large, because there are required in inspection process professional knowledge and special skills such as suspension, dilution, application, colony measurement and the like.

Moreover, it is required to dye cells by hand work of a tester when a device utilizing the fluorescence flow cytometry method is used. Moreover, measurement results are influenced by the skill of a tester because the dyeing operation requires addition of a predetermined quantity of a dyeing reagent, and quick measurement after dyeing.

Furthermore, there is easily generated the surplus of a reagent used for dyeing. As a little amount of a dyeing reagent is required for one specimen, there is a surplus of prepared dyeing reagents when there is a few specimens to be measured. Surplus dyeing reagents are often disposed in order to prevent deterioration effects. Accordingly, a larger quantity of reagents than an originally required amount is needed to increase the cost.

Furthermore, as dyeing reagents for cells and bacteria are often harmful for a human body, there may be not excluded a possibility that a tester is exposed to a dyeing reagent when the dyeing operation is performed by hand working.

Furthermore, a cost for manufacturing a flow path producing a laminar flow is very high because the flow path is a complex glasswork for longer use.

Hereinafter, embodiments according to the present invention will be explained, referring to drawings.

Figure 1A:
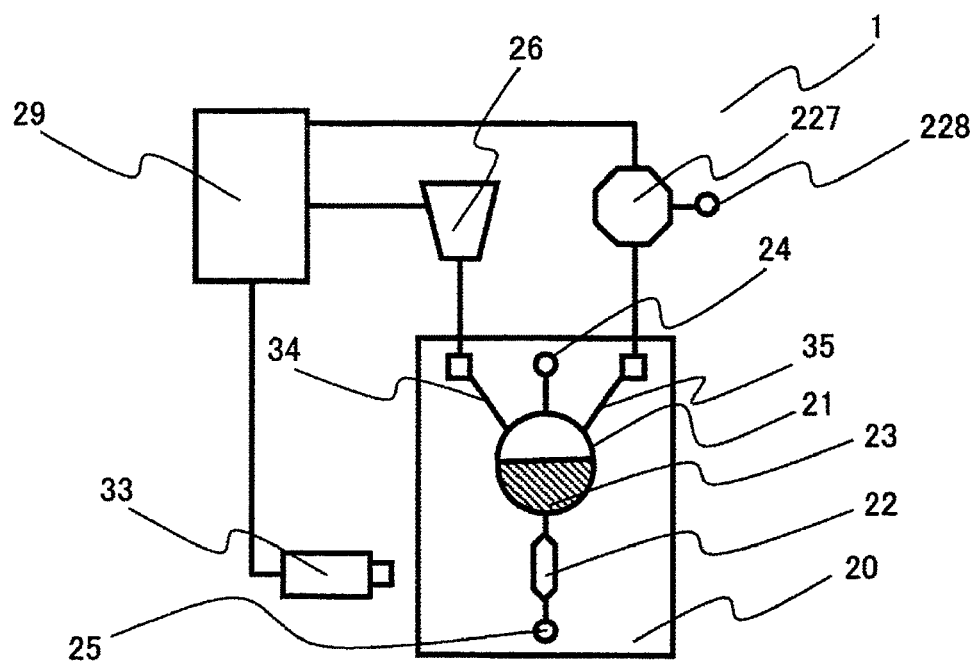
FIG. 1A is a block diagram showing a microorganism testing device according to one embodiment of the present invention.

FIG. 1A is a view showing a basic system of a microorganism testing device 1. The microorganism testing device 1 includes: a measurement chip 20; a fluid feeding means 26 for feeding liquid in the measurement chip 20; a flow path opening and closing means 227 for letting air in the measurement chip 20 escape; a flow-type fine-particle detection means 33 for detecting a bacteria flowing in the measurement chip 20; and a control means 29 for controlling the fluid feeding means 26, the flow path opening and closing means 227, and the flow-type fine-particle detection means 33.

The measurement chip 20 includes; a reaction container 21 for holding a dyeing reagent 23 which dyes bacteria in a specimen, and mixing the specimen and the dyeing reagent 23; a detection flow path 22 as a flow path which is connected to the reaction container 21 and detects bacteria in the flowing specimen; a specimen inlet port 24 for introducing a specimen into the measurement chip 20; a communicating flow path 34 for connecting the reaction container 21 and the fluid feeding means 26; a communicating flow path 35 for connecting the reaction container 21 and the flow path opening and closing means 227; and a waste fluid port 25 which is connected to the detection flow path 22, and discards liquid mixture of the specimen and the dyeing reagent 23.

When the specimen is introduced into the measurement chip 20, the flow path opening and closing means 227 opens a ventilation port 228 to let gas in the reaction container 21 escape. Accordingly, liquid mixture of the specimen and the dyeing reagent 23 is prevented from flowing into the detection flow path 22. After completing mixture of the specimen and the dyeing reagent 23, the flow path opening and closing means 227 closes the ventilation port 228, and, through the fluid feeding means 26, the liquid mixture of the specimen and the dyeing reagent 23 flows to the detection flow path 22. The bacteria which flow in the detection flow path 22 are detected by the flow-type fine-particle detection means 33.

Figure 1B:
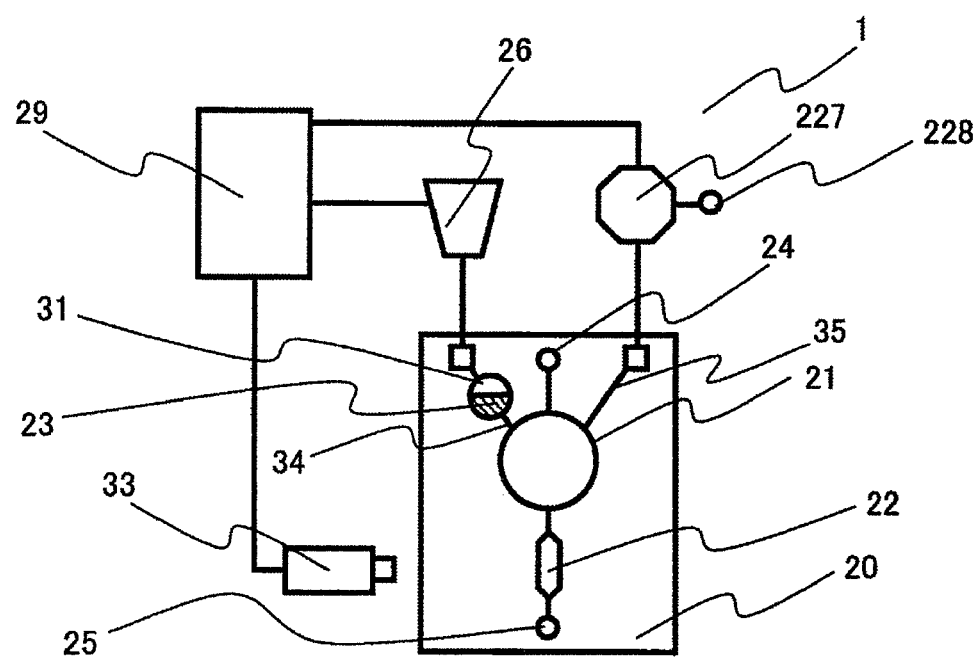
FIG. 1B is a block diagram showing a microorganism testing device according to one embodiment of the present invention.

FIG. 1B is a view showing a basic system of the microorganism testing device 1 when the dyeing reagent 23 is held in another container. A reagent container 31 holding the dyeing reagent 23 is provided in the communicating flow path 34 connecting the reaction container 21 and the fluid feeding means 26.

The fluid feeding means 26 flows the dyeing reagent 23 from the reagent container 31 to the reaction container 21. At this time, the flow path opening and closing means 227 opens the ventilation port 228 to let gas in the reaction container 21 escape. Accordingly, liquid mixture of the specimen and the dyeing reagent 23 is prevented from flowing into the detection flow path 22.

Hereinafter, examples of the microorganism testing device 1 will be described, based on the present view showing the basic system.

EXAMPLE 1

A measurement chip 10 is used for measuring bacteria in liquid, such as drinking water and juice, including very few residual foods wherein the measuring is performed, using one k ind of a dyeing reagent.

Figure 2:
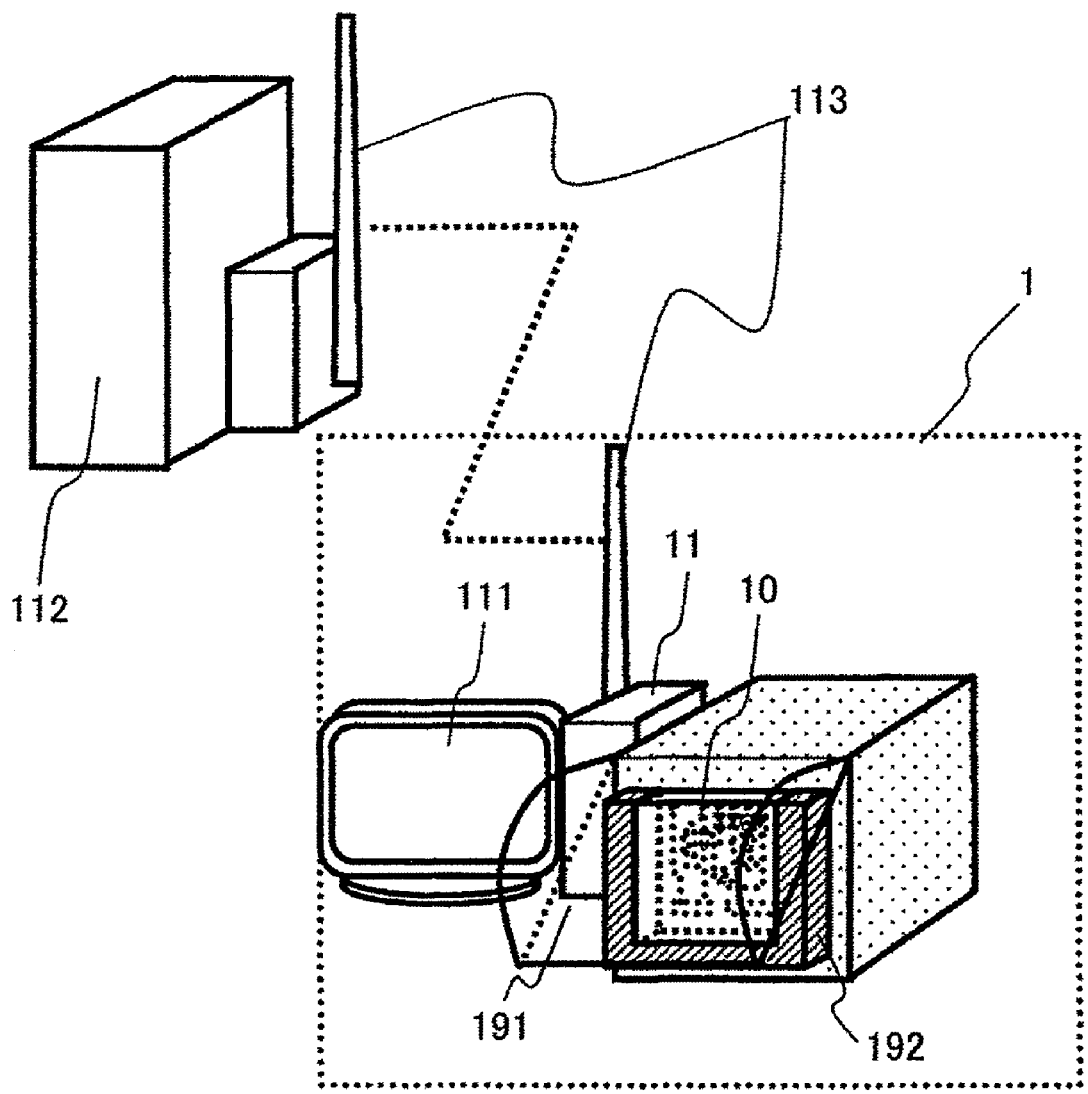
FIG. 2 is a schematic view showing a microorganism testing device according to one embodiment of the present invention.

FIG. 2 is a schematic view of the microorganism testing device 1. The microorganism testing device 1 is used in a state in which the measurement chip 10 is set in a holder 192. The measurement chip 10 is fixed to the side of the microorganism testing device 1, using the holder 192 and a lid 191. An optimal process for measurement of the number of bacteria may be executed according to various kinds of specimens by changing the kind of the set measurement chip 10. A system device 11 performs control of the microorganism testing device 1, and processing of electric signals output from the microorganism testing device 1, and an output device 111 outputs obtained inspection results.

Moreover, the system device 11 exchanges data with a server 112 through a communication device 113. The server 112 collects output results from a plurality of microorganism inspection devices 1 through the communication device 113 for analysis. Moreover, in order to execute an optimal process for measurement of the number of bacteria according to the kinds of specimens, the server 112 transmits an optimal control method of the microorganism testing device 1 to a plurality of microorganism testing devices 1 through the communication device 113.

Figure 3:
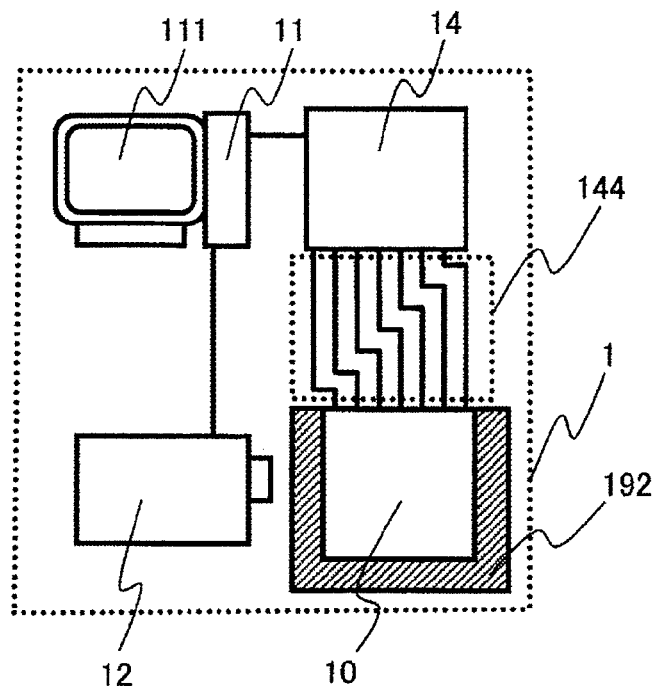
FIG. 3 is a configuration diagram showing a microorganism testing device according to one embodiment of the present invention.

FIG. 3 is a configuration diagram of the microorganism testing device 1. The microorganism testing device 1 includes: a measurement chip 10 which holds a specimen and a dyeing reagent therein, and is provided with a mechanism executing processes necessary for measuring bacteria; the holder 192 which holds the measurement chip 10 and has a function controlling the temperature of the measurement chip 10; a delivery device 14 for control of delivering a specimen and a dyeing reagent in the measurement chip 10 through a chip connecting tube 144 connected to the measurement chip 10 in order to execute processes necessary for measuring bacteria; and a detection device 12 which irradiates bacteria in the measurement chip 10 with excitation light and converts fluorescence from the bacteria into electric signals. The system device 11 connected to the microorganism testing device 1 outputs control signals to the delivery device 14 and the holder 192, and processes electric signals from the detection device 12. The measurement results obtained by processing of electric signals are displayed on an output device 111.

Figure 4:
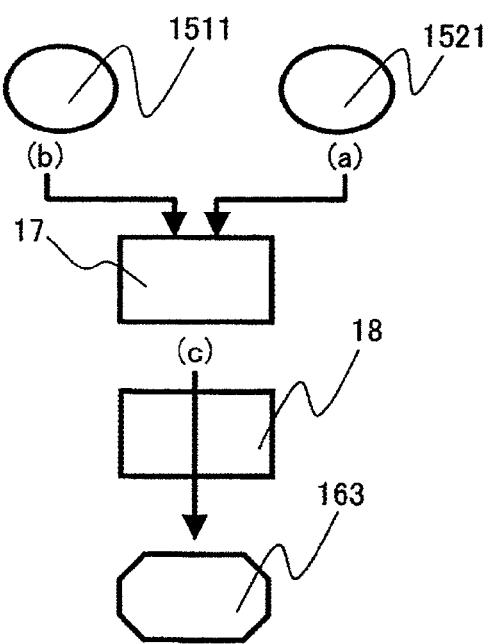
FIG. 4 is a process drawing for a microorganism testing device according to one embodiment.

FIG. 4 is a process drawing for measurement of bacteria in the measurement chip 10. The measurement chip 10 is provided with: a reaction container 17 for dyeing of a specimen 1511 with a dyeing reagent 1521; a bacteria detection portion 18 for detection of a bacteria; and a detection liquid waste container 163 to maintain the liquid mixture of two liquids for which detection operation is completed. A symbol (a) in the drawing indicates a processing path of the specimen 1511, and a symbol (b) in the drawing indicates a processing path of the dyeing reagent 1521. Processes for measuring bacteria will be explained.

1. The dyeing processes of bacteria in the specimen are performed according to the processing paths indicated by symbols (a) and (b). The dyeing reagent 1521, and the specimen 1511 is input into the reaction container 17 for mixing the two liquids. The bacteria in the specimen are dyed with the dyeing reagent 1521. During time required for dyeing, the liquid mixture of two liquids is held in the reaction container 17. The order in which the specimen 1511 and the dyeing reagent 1521 are input into the reaction container 17 is not limited, and it is acceptable for either of them to be input into the reaction container 17 beforehand.

2. The process for measurement of bacteria dyed with a fluorochrome is executed according to the processing path indicated by a symbol (c). After time required for dyeing passes, the liquid mixture of two liquids is input into the bacteria detection portion 18. In the bacteria detection portion 18, bacteria in the liquid mixture are measured. After the measurement in the bacteria detection portion 18 is completed, the liquid mixture is input into the detection liquid waste container 163.

As all the above-described processes are performed in the measurement chip 10, the risk that a tester contacts with bacteria in the specimen 1511 and a dyeing reagent 1521 is reduced, and there is caused less influence on inspection results by human errors of the tester and by external influences.

FIG. 5 through FIG. 13 are views explaining details of each process for measurement of bacteria. The dyeing process and the measurement process for bacteria will be explained in this order.

Figure 5:
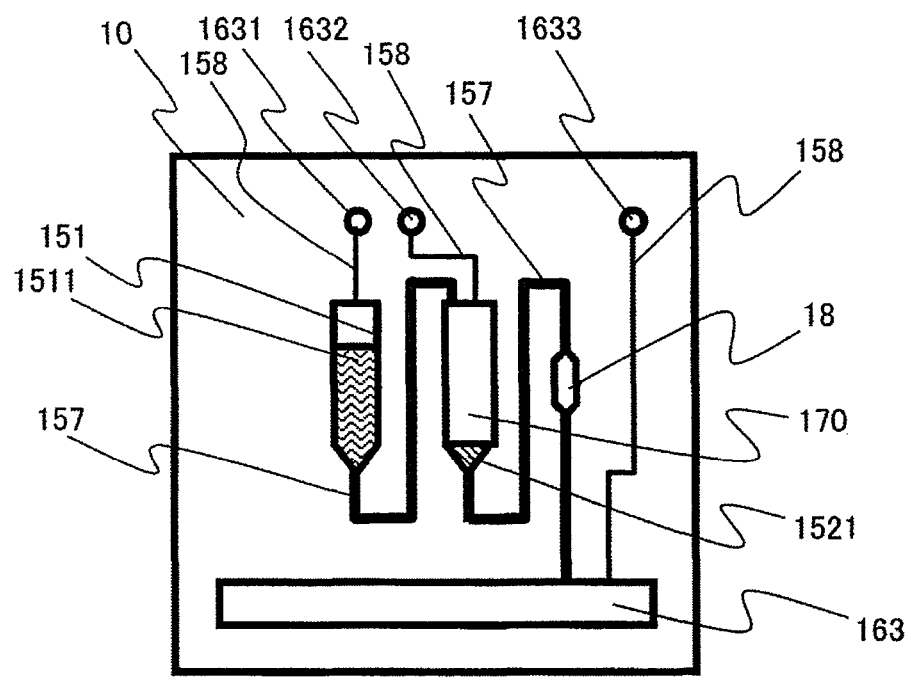
FIG. 5 is a plan view showing a measurement chip in a microorganism testing device according to one embodiment.

FIG. 5 is a plan view of the measurement chip 10. The measurement chip 10 includes: a specimen container 151 holding the specimen 1511; a reaction container 170 mixing the specimen 1511 and the dyeing reagent 1521 for reaction;

the bacteria detection portion 18; the detection liquid waste container 163 into which the liquid mixture of the specimen 1511 and the dyeing reagent 1521, which have passed the bacteria detection portion 18, enters; a solution flow path 157 which connects the specimen container 151, the reaction container 170, and the bacteria detection portions 18, and in which the specimen 1511 and the liquid mixture flow; ventilation ports 1631 through 1633 by which the specimens 1511 and the liquid mixture in each container flow by the atmospheric pressure; and an air flow path 158 connecting each of the ventilation ports 1631 through 1633 and its corresponding container.

The design has been made in such a way that the depth and width of the solution flow path 157 are within a range of 10 μm through 1 mm, the depth and width of the air flow path 158 are within a range of 10 μm through 1 mm, and the sectional area of the solution flow path 157 is larger than that of the air flow path 158.

The dyeing reagent 1521 is encapsulated beforehand in the reaction container measurement chip 10. Accordingly, deterioration effects caused by external environments, and a possibility that a tester is exposed to a dyeing reagent are controlled to the minimum. The specimen 1511 is injected from the ventilation port 1633 into the specimen container 151 before testing.

The volume of the specimen container 151 is larger than that of the specimen 1511, and the volume of the reaction container 170 is larger than the total volume of the specimen 1511 and the dyeing reagent 1521. Moreover, the highest point of the solution flow path 157 connecting the specimen container 151 and the reaction container 170 is designed to be higher than the water level of the specimen 1511 in the specimen container 151, and, similarly, the highest point of the solution flow path 157 connecting the reaction container 170 and the bacteria detection portion 18 is designed to be higher than the water level of the liquid mixture of the specimen 1511 and the dyeing reagent 1521 in the reaction container 170.

A pigment for dyeing bacteria such as a DAPI (1 μg/mg through 1 mg/ml), an acridine orange (1 μg/mg through 1 mg/ml), an ethidium bromide (1 μg/ml through 1 mg/ml), a SYTO (1 μg/ml through 1 mg/ml), and the like are used as the dyeing reagent.

Figure 6:
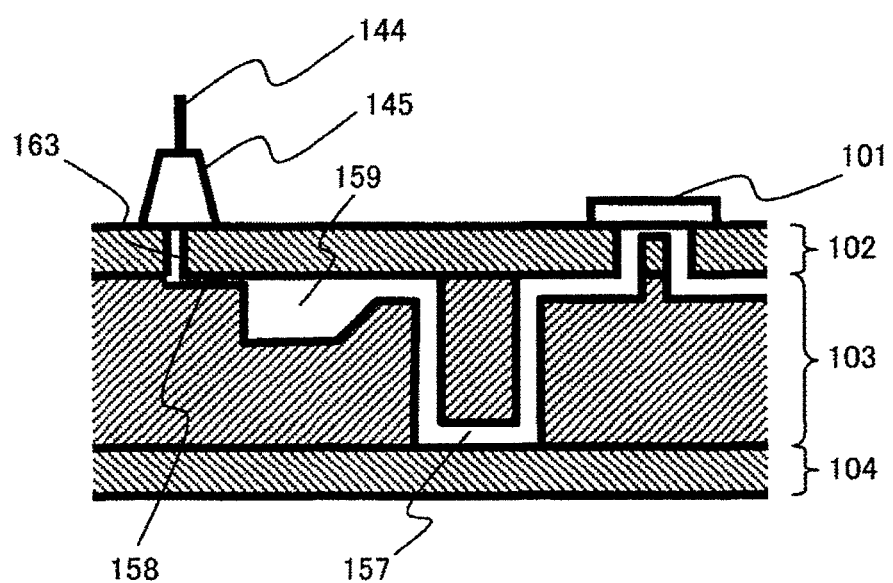
FIG. 6 is a cross sectional view of the measurement chip shown in FIG. 5.

FIG. 6 is a cross sectional view showing a structure of the measurement chip. The measurement chip 10 has a four-layer structure including: a measurement member 101 formed of an optically transparent material such as glass, quartz, polymethacrylate, and a PDMS; an upper member 102; an intermediate member 103, and a lower member 104. In order to prevent deterioration of the dyeing reagent 1521 by external light, it is preferable to use a member obtained by light shielding processing of a material such as a polymethacrylate, an ABS, a polycarbonate, and a PDMS as the upper member 102, the intermediate member 103, and the lower member 104.

The intermediate member 103 has trenches on the surfaces on which the upper member 102 and the lower member 104 are glued. By gluing the upper member 102, the intermediate member 103 and the lower member 104 together, a deep trench forms a container 159 for holding the specimen and the reagents, and a shallow trench forms both the solution flow path 157 in which the specimen and the reagents flow, and the air flow path 158 in which air flows. The flow paths formed on the both sides of the intermediate member 103 are connected through a through hole.

The upper member 102 has a trench on the surface contacting the measurement member 101, and is also provided with through holes. A detection flow path 181 optically-measurable from the outside is formed by gluing the upper member and the measurement member together. Fluorescence from bacteria dyed with a fluorochrome may be measured through the measurement member 101. The through holes form the ventilation port 163 and a flow path for connecting the detection flow path 181 and the solution flow path 157. The ventilation port 163 is connected to the delivery device 14 through a fitting 145 at the end of the chip connecting tube 144 (FIG. 3).

Figure 7:
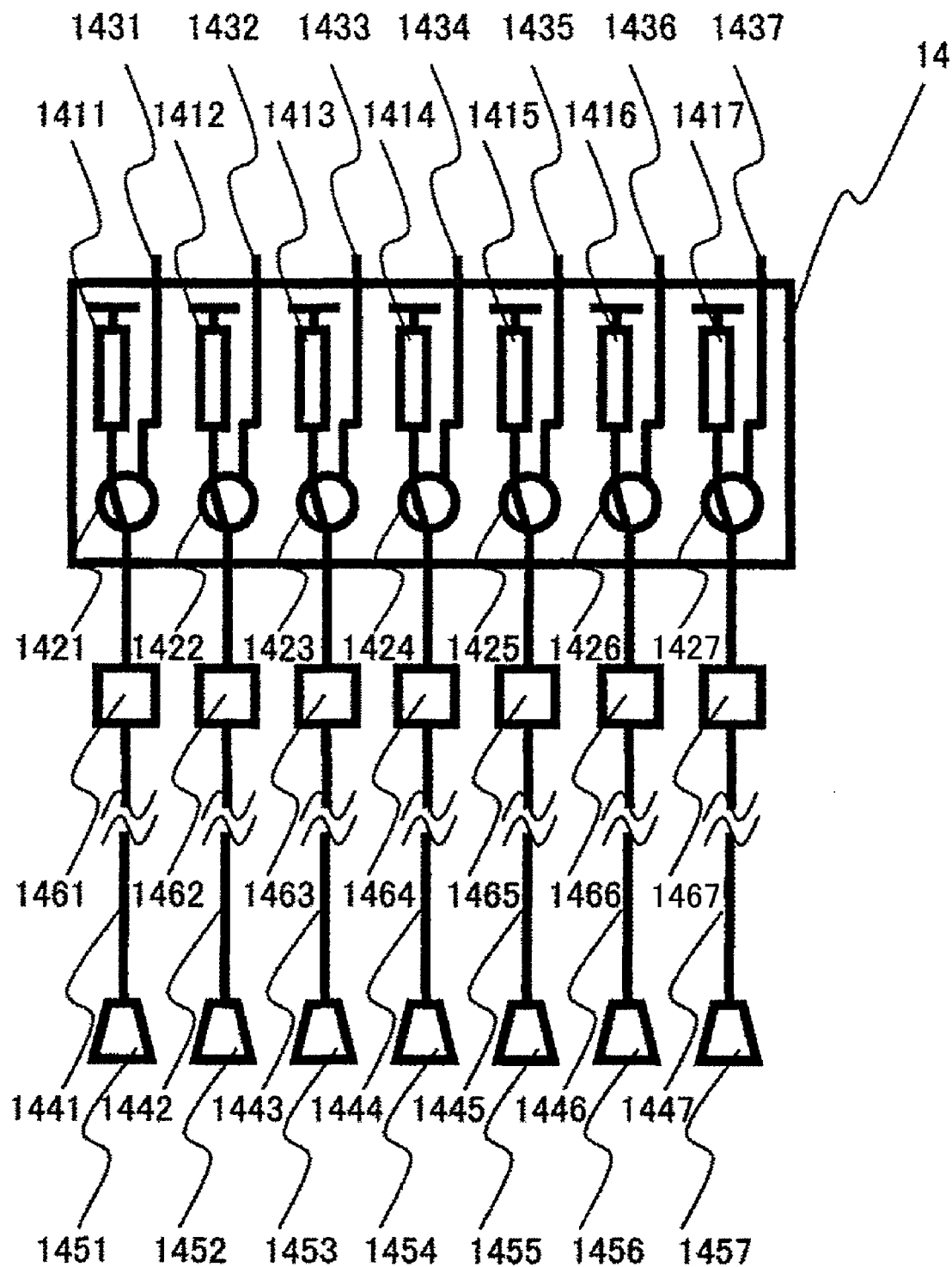
FIG. 7 is a configuration diagram showing a delivery device in a microorganism testing device according to one embodiment.

FIG. 7 is a configuration diagram of the delivery device 14 in FIG. 3. The delivery device 14 includes: pumps 1411 through 1417 for setting air pressure in their respective chip connecting tubes 1441 through 1447 higher than the atmospheric pressure; valves 1421 through 1427; ventilation ports 1431 through 1437 which are open to the air; chip connecting tubes 1441 through 1447; fittings 1451 through 1457 for connecting their respective chip connecting tubes 1441 through 1447 with the measurement chip 10; and pressure sensors 1461 through 1467 for measuring air pressures of their respective chip connecting tubes 1441 through 1447.

It is possible to set the pressure in the chip connecting tubes 1441 through 1447 equal to or higher than the atmospheric pressure by switching their respective valves 1421 through 1427 to their respective ventilation ports 1431 through 1437 or their respective pumps 1411 through 1417. The flow of the specimen 1511 and each of the reagents in the measurement chip 10 may be controlled by control of the air pressure of the chip connecting tubes 1441 through 1447. The number of chip connecting tubes 1441 through 1447, which are connected to the measurement chip, may be changed according to the kind of the measurement chip used.

Figure 8:
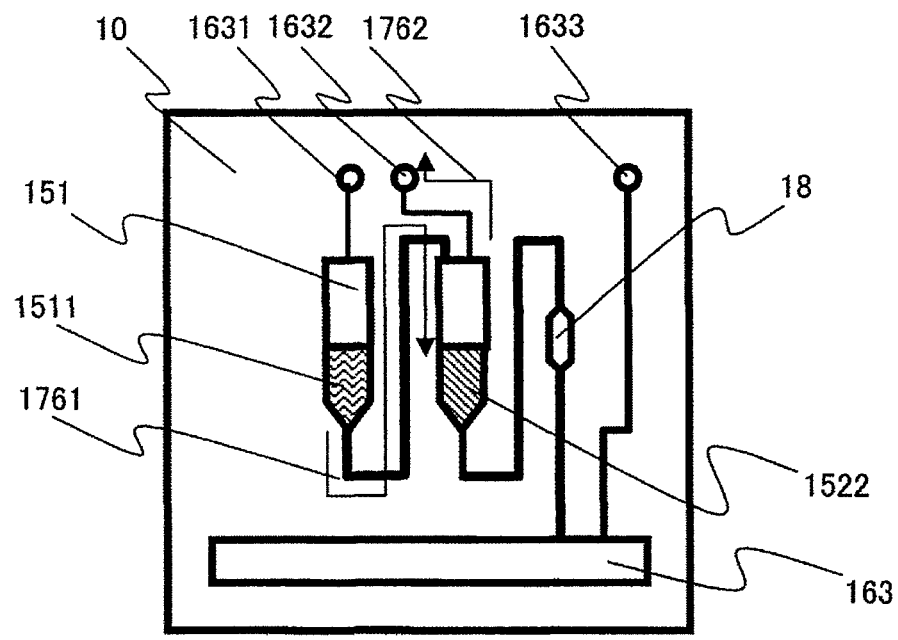
FIG. 8 is a plan view showing the flowing state of a specimen in a measurement chip according to one embodiment.

FIG. 8 is a view showing the flow of the specimen 1511 in the measurement chip 10 in the process for dyeing the specimen 1511 with the dyeing reagent 1521.

The air pressure in the specimen container 151 is increased by applying pressure thereto from the delivery device 14 (FIG. 6) through the ventilation port 1631. At the same time, the reaction container 170 and the detection liquid waste container 163 are opened to the atmosphere through the ventilation ports 1632 and 1633. According to the pressure difference, the specimen 1511 is input into the reaction container 170 along the arrow 1761 for mixing with the dyeing reagent 1521. Flow velocity may be kept constant by monitoring the difference in the air pressure with the pressure sensors 1461 through 1467 of the delivery device 14. As the pressure of the specimen container 151 becomes the atmospheric pressure when the whole quantity of the specimen 1511 flows in the reaction container 170, the delivery state may be monitored using the pressure sensors 1461 through 1467.

The water level of the liquid mixture of two liquids does not exceed the highest point of the solution flow path 157 connecting the reaction container 170 and the bacteria detection portion 18, and air in the reaction container 170 is discharged to the outside along the arrow 1762 through the ventilation port 1632. Thereby, the liquid mixture of two liquids is not pushed out to the bacteria detection portion 18, and the liquid mixture is held in the reaction container 170 during time required for the reaction. At this time, in order to further prevent the liquid mixture from flowing into the bacteria detection portion 18, pressure from the delivery device 14 is applied to the detection liquid waste container 163 through the ventilation port 1633, and it is acceptable to increase the air pressure of the detection liquid waste container 163 to a range lower than the pressure of the specimen container 151.

Here, the influence on dyeing by a change in the temperature is reduced by keeping the temperature of the measurement chip 10 constant by the holder 192 (FIG. 2) during dyeing.

Figure 9:
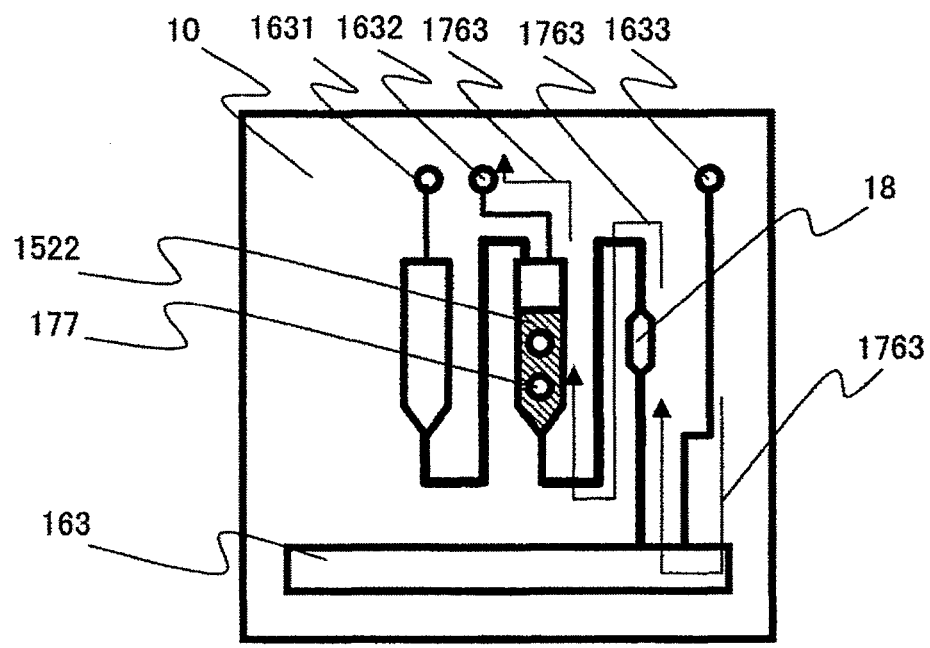
FIG. 9 is a plan view showing a state in which a specimen is stirred in a measurement chip according to one embodiment.

FIG. 9 is a view showing operations for promoting the mixture of the two liquids after mixing of the specimen 1511 and the dyeing reagent 1521. Pressure from the delivery device 14 is applied to the detection liquid waste container 163 through the ventilation port 1633 to increase the pressure of the container 163 to within a range lower than the pressure of the specimen container 151. At the same time, the reaction container 170 and the specimen container 151 are open to the atmosphere pressure through ventilation port 1631 and the ventilation port 1632. Air flows into the reaction container 170 along the arrow 1763. Air becomes bubbles 177, and, when the bubbles rise from the bottom to the top of a liquid mixture 1522, the liquid mixture 1522 is stirred for promoting the mixture.

Figure 10:
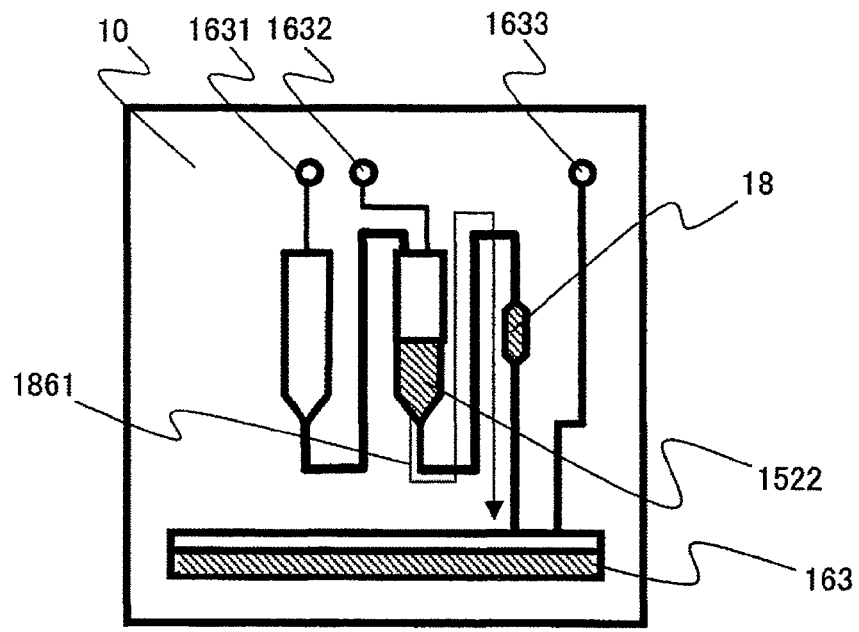
FIG. 10 is a plan view showing a flow state of liquid mixture in a measurement chip according to one embodiment.

FIG. 10 is a view showing the flow of the liquid mixture 1522 in the measurement chip 10 in the measurement process of bacteria. Pressure from the delivery device 14 is applied to the reaction container 170 through the ventilation port 1632 to increase the pressure in the reaction container 170. At the same time, the detection liquid waste container 163 is opened to the air through the ventilation port 1633. Other ventilation ports 1631 are closed. According to the atmospheric pressure difference, the liquid mixture 1522 flows from the reaction container 170 to the detection liquid waste container 163 through the bacteria detection portion 18. The bacteria in the liquid mixture 1522 is measured when the bacteria passes through the bacteria detection portion 18. The measurement of the bacteria in the bacteria detection portion 18 is performed by using the fluorescence flow cytometry method.

Figure 11:
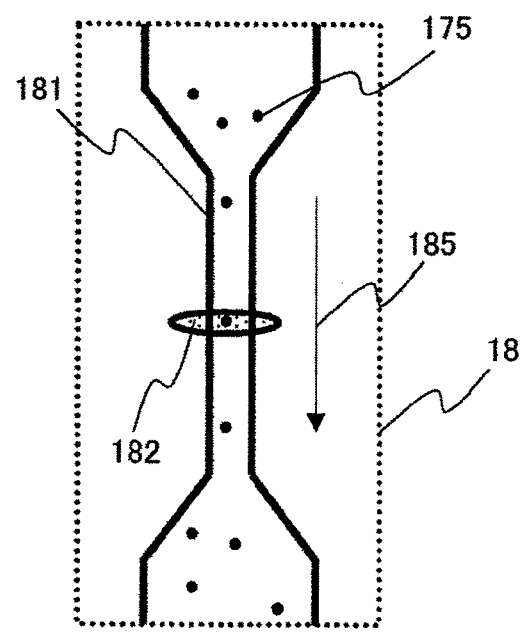
FIG. 11 is an enlarged plan view of a bacteria detection portion in a measurement chip according to one embodiment.
Figure 12:
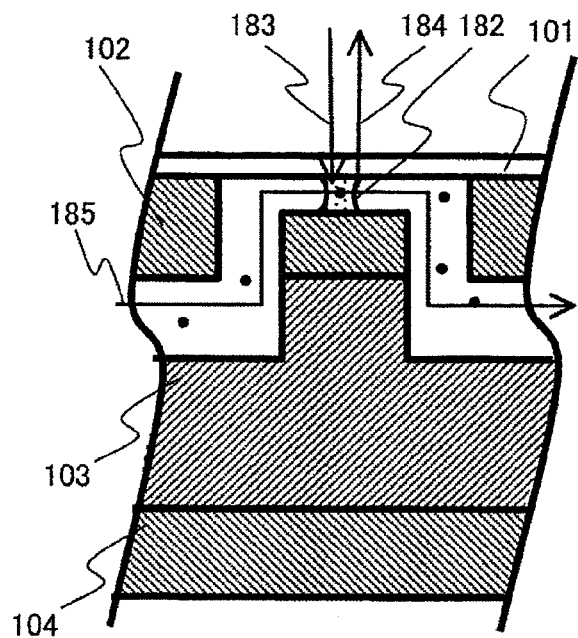
FIG. 12 is an enlarged cross sectional view of a bacteria detection portion in a measurement chip according to one embodiment.

FIG. 11 is an enlarged plan view of the bacteria detection portion 18, and FIG. 12 is an enlarged cross sectional view of the portion 18. The detection flow path 181 in the bacteria detection portion 18 is designed in such a way that the flow path width and depth are 0.1 μm through 0.1 mm, and the length is within a range of 10 μm through 10 mm, and is longer than the flow path width and depth. Moreover, the sectional area of the detection flow path 181 is smaller than that of the solution flow path 157. Accordingly, two or more bacteria seldom flow side by side because the flow path is very narrow.

Excitation light 183 from the detection device 12 enters the detection flow path 181 for detection of bacteria, after passing through the measurement member 101. The excitation light 183 is condensed into an elliptical shape in the detection device 12 (FIG. 2), and the excitation light 183 is narrowed to an irradiation range 182. The dyed bacteria 175 flows along the arrow 185, and produces fluorescence 184 when the cell 175 passes through the irradiation range 182. The fluorescence 184 which has passed the measurement member 101 is detected by the detection device 12.

Figure 13:
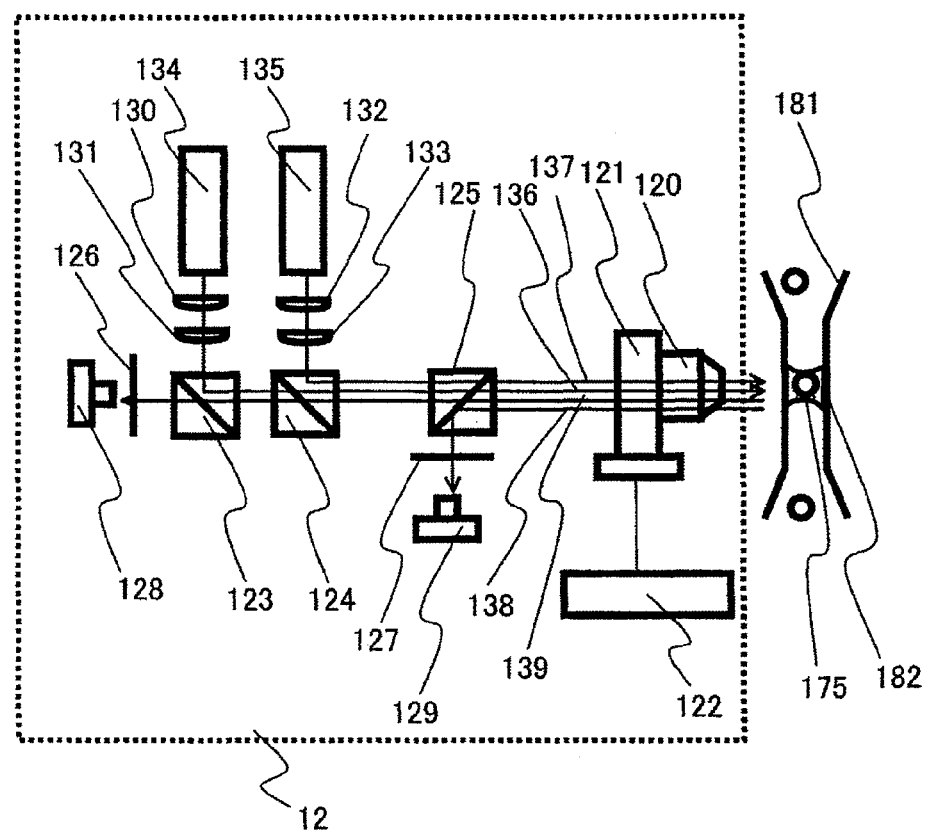
FIG. 13 is a configuration diagram showing a detection device in a microorganism testing device according to one embodiment.

FIG. 13 is a configuration diagram of an optical system of the detection device 12. In some cases, an optical device and its arrangement depend on both excitation spectra and fluorescent spectra of dyeing pigments used. Here, an optical system suitable for use of two kinds of dyeing pigments, that is, ethidium bromide (the excitation wavelength: 520 nm, and the fluorescent wavelength: 615 nm), and DAPI (the excitation wavelength: 360 nm, and the fluorescent wavelength: 460 nm) will be explained.

The detection device 12 includes: a short wavelength laser 134 (wavelength 360 nm) as an excitation light source with a short wavelength (for DAPI); a long wavelength laser 135 (wavelength 520 nm) as an excitation light source with a long wavelength (for ethidium bromide); cylindrical lenses 130 through 133 for condensing laser light from each laser into elliptical shapes; a short wavelength dichroic mirror 123 for reflecting light with a wavelength of 400 nm or less; a medium-wavelength dichroic mirror 124 for reflecting light with a wavelength of 500 nm or more; a long-wavelength dichroic mirror for reflecting light with a wavelength of 600 nm or more; a short wavelength optical filter 126 which does not transmit light with a wavelength of 500 nm or more; a long wavelength optical filter 127 which does not transmit light with a wavelength of 700 nm or more; a short wavelength photomultiplier 128 for detecting light which has passed through the short wavelength optical filter 126; a long wavelength photomultiplier 129 for detecting light which has passed through the long wavelength optical filter 127; an object lens 120 for condensing fluorescence from the bacteria 175; a piezo 121 which moves the object lens 120 at high speed in order to expand the range of focal depth; and a piezo controller 122 which controls the action of the piezo.

The excitation light 136 (wavelength 360 nm) output from the short wavelength laser 134 is condensed into an elliptical shape by the cylindrical lenses 130 and 133, is reflected on the short wavelength dichroic mirror 123, passes through the medium-wavelength dichroic mirror 124, a long-wavelength dichroic mirror 125, and the object lens 120, and excites DAPI having dyed the bacteria 175 which flows in the irradiation range 182. The fluorescence 139 (wavelength 460 nm) from the DAPI enters the short wavelength photomultiplier 128, after passing through the long-wavelength dichroic mirror 125, the medium-wavelength dichroic mirror 124, the short wavelength dichroic mirror 123 and the short wavelength optical filter 126. The fluorescence 139 detected by the short wavelength photomultiplier 128 is converted into an electric signal, and the electric signal is sent to the system device 11. On the other hand, excitation light 137 (wavelength 530 nm) output from the long wavelength laser 135 is condensed into an elliptical shape by the cylindrical lenses 132 and 133, is reflected on the medium-wavelength dichroic mirror 124, passes through the long-wavelength dichroic mirror 125 and the object lens 120, and excites ethidium bromide which has dyed the bacteria 175 which flows in the irradiation range 182. Fluorescence 138 (wavelength 620 nm) from the ethidium bromide is reflected on the long-wavelength dichroic mirror 125, passes through the long wavelength optical filter 127, and enters the long wavelength photomultiplier 129. The fluorescence 138 detected by the long wavelength photomultiplier 129 is converted into an electric signal, and the electric signal is sent to the system device 11. The system device 11 processes the electric signals sent from the short wavelength photomultiplier 128 and the long wavelength photomultiplier 129, and outputs information on the number of bacteria as an inspection result to the output device 111.

Figure 14:
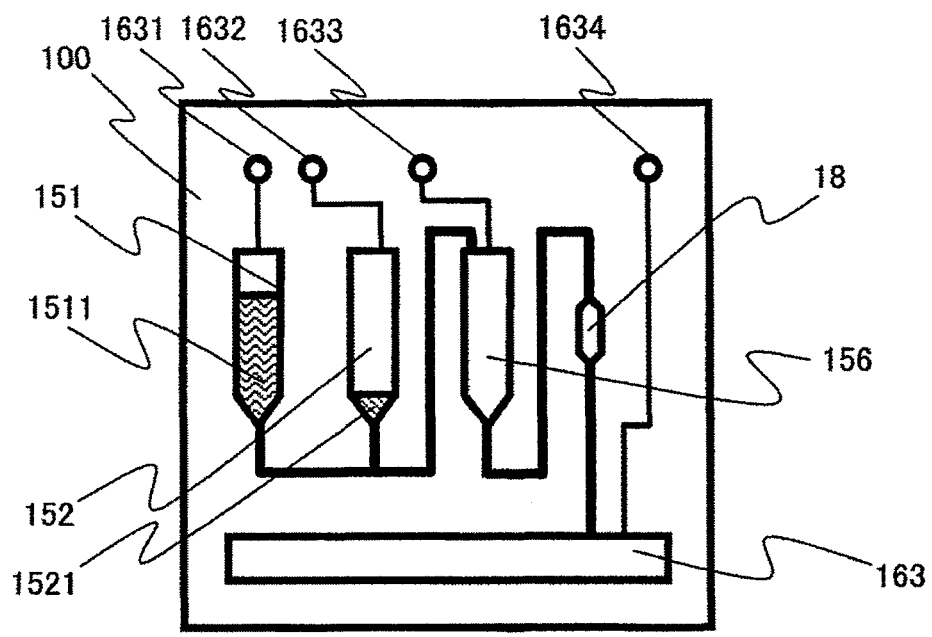
FIG. 14 is a plan view of a measurement chip according to another embodiment of the present invention.

FIG. 14 is a plan view of a measurement chip 100, and the chip 100 is used instead of the measurement chip 10. The measurement chip 100 has a structure in which the specimen 1511 and the dyeing reagent 1521 are flown into the reaction container 170, and bacteria in the liquid mixture of two liquids are detected in the bacteria detection portion 18. As mixing of two liquids is promoted by flowing two liquids in the reaction container at the same time, the above mixing is effective when there is a large difference in specific gravity between the dye liquid and the specimen.

When the specimen 1511 and the dyeing reagent 1521 are flown into the reaction container 170, pressure from the delivery device 14 is applied to the specimen container 151 through the ventilation port 1631 and the dyeing reagent container 152 through the ventilation ports 1632 to increase the pressure in the specimen container 151 and that in the dyeing reagent container 152. At the same time, the reaction container 170 and the detection liquid waste container 163 are opened to the air through the ventilation port 1633 and ventilation port 1634 respectively. The specimen 1511 and the dyeing reagent 1521 enter the reaction container 170 to mix each other, based on the difference in pressure.

The water level of the liquid mixture of two liquids does not exceed the highest point of the solution flow path 157 connecting the reaction container 170 and the bacteria detection portion 18, and, furthermore, air in the reaction container is discharged to the outside through the ventilation port 1633. As the pressure of the reaction container 170 is equal to the atmospheric pressure, the liquid mixture of two liquids is not pushed out to the bacteria detection portion 18, and the liquid mixture may be held in the reaction container 170 during time required for the reaction. At this time, further in order to prevent the liquid mixture from flowing into the bacteria detection portion 18, it is acceptable to increase the pressure of the detection liquid waste container 163 to within a range lower than the pressure of the specimen container 151 by applying the pressure from the delivery device 14 to the container 163 through the ventilation port 1633.

As, according to the present example, all processes from dyeing of bacteria in the specimen to measurement of the number of cells may be performed in one disposable chip, work load of a tester, and a risk that a tester is exposed to a dyeing reagent are reduced. Thereby, the influence of tester skill on measurement results becomes small to obtain stable measurement results.

EXAMPLE 2

There will be described an example using a measurement chip 100 in which viable bacteria and killed bacteria in liquid including a few residual foods such as drinking water and juice, are measured using two kinds of dyeing reagents.

The number of viable bacteria in a specimen may be measured by dyeing the cells in different colors with different dyeing pigments. Dyeing killed bacteria and viable bacteria in different colors is performed in such a way that killed bacteria dyeing pigment which dyes a killed bacterium are added to a specimen, and viable-and-killed bacteria dyeing pigment which dyes killed-and-viable bacteria are added after a predetermined time.

Figure 15:
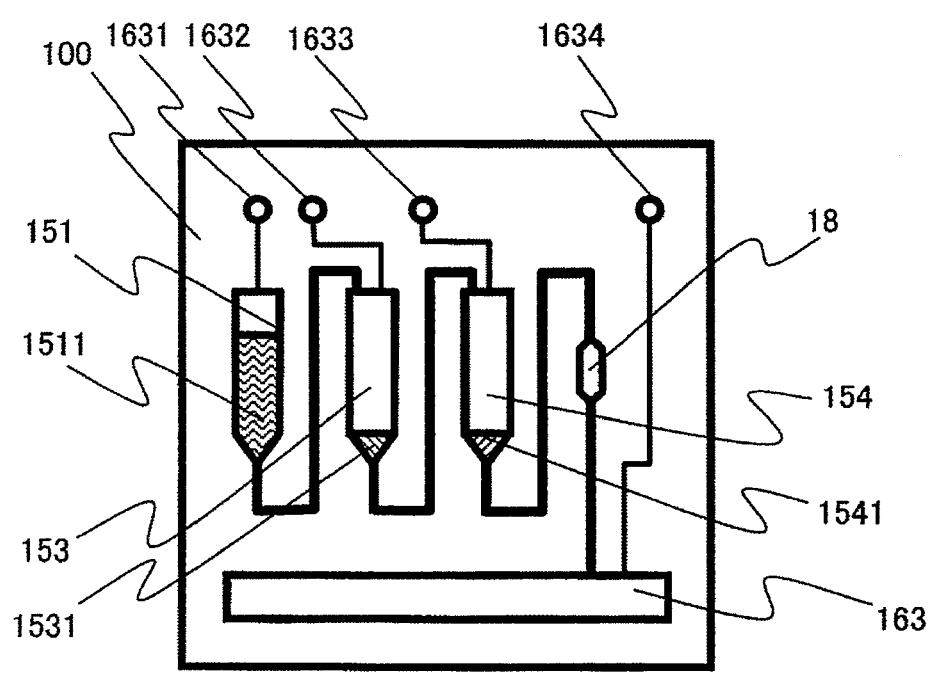
FIG. 15 is a plan view of a measurement chip according to further another embodiment of the present invention.

FIG. 15 is a plan view of a measurement chip 20. The measurement chip 20 has a structure in which another reaction container is added to the measurement chip 10 (FIG. 5). Among two reaction containers, a reaction container for holding killed bacteria dyeing pigment 1531 is assumed to be a killed bacteria dyeing reagent holding container 153, and a reaction container for holding viable-and-killed bacteria dyeing pigment 1541 is assumed to be a viable-and-killed bacteria dyeing pigment holding container 154. The specimen container 1511, the killed bacteria dyeing reagent holding container 153, the viable-and-killed bacteria dyeing reagent holding container 154, the bacteria detection portion 18, and the detection liquid waste container 163 are connected in series through the solution flow path 157.

For example, PI (prosium iodide) (1 µg/ml through 1 mg/ml) is used as the killed bacteria dyeing reagent 1531, and DAPI (1 µg/ml through 1 mg/ml) is used as the viable-and-killed bacteria dyeing reagent 1541.

Hereinafter, an operation in which killed bacteria and viable bacteria are detected in the measurement chip 20 will be explained.

1. The specimen 1511 flows to the killed bacteria dyeing reagent holding container 153. Pressure from the delivery device 14 is applied to the specimen container 151 through the ventilation port 1631 to increase the air pressure in therein. At the same time, the killed bacteria dyeing reagent holding container 153, the viable-and-killed bacteria dyeing reagent holding container 154, and the detection liquid waste container 163 are opened to the air through their respective ventilation ports 1632 through 1634. The specimen 1511 enters the killed bacteria reagent holding container 153 by the pressure difference, to mix with the killed bacteria dyeing reagent 1531. The killed bacteria in the specimen 1511 are dyed with the killed bacteria dyeing reagent 1531.

On the other hand, viable bacteria in the specimen 1511 are not dyed. The water level of the liquid mixture of two liquids does not exceed the highest point of the solution flow path 157 connecting the killed bacteria reagent holding container 153 and viable-and-killed bacteria dyeing reagent holding container 154, and, furthermore, air in the reaction container is discharged to the outside through the ventilation port 1632. As the pressure of the killed bacteria reagent holding container 153 is equal to the atmospheric pressure, the liquid mixture of two liquids is not pushed out to the viable-and-killed bacteria dyeing reagent holding container 154, and the liquid mixture may be held in the killed bacteria reagent holding container 153 during time required for the reaction. Similarly, the viable-and-killed bacteria dyeing reagent holding container 154 is not pushed out to the bacteria detection portion 18, and does not flow backward to the killed bacteria reagent holding container 153.

At this time, further in order to prevent the liquid mixture from flowing into the viable-and-killed bacteria dyeing reagent holding container 154, it is acceptable to increase the pressure of the viable-and-killed bacteria dyeing reagent holding container 154 to within a range lower than the pressure of the specimen container 151 by applying the pressure from the delivery device 14 to the viable-and-killed bacteria dyeing reagent holding container 154 through the ventilation port 1633, and to increase the pressure of the detection liquid waste container 163 to within a range lower than the pressure of the specimen container 151 by applying the pressure from the delivery device 14 to the container 163 through the ventilation port 1634. Recommendably, the influence on dyeing by a change in the temperature is reduced by keeping the temperature of the measurement chip 20 constant during dyeing, using the holder 192 (FIG. 2).

2. The liquid mixture of the specimen 1511 and the killed bacteria dyeing reagent 1531 is flown into the viable-and-killed bacteria dyeing reagent holding container 154. The viable-and-killed bacteria dyeing reagent 1541 is added to the specimen 1511, and killed bacteria and viable bacteria in the specimen 1511 are dyed with the viable-and-killed bacteria dyeing reagent 1541.

3. The liquid mixture of the specimen 1511, the killed bacteria dyeing reagent 1531, and the viable-and-killed bacteria dyeing reagent 1541 are flown into the bacteria detection portion 18. As only the fluorescence of the viable-and-killed bacteria dyeing reagent 1541 is detected for viable bacteria, and the fluorescence of the viable-and-killed bacteria dyeing reagent 1541 and that of the killed bacteria dyeing reagent 1531 are detected for killed bacteria in the bacteria detection portion 18, distinction between the viable bacteria and the killed bacterial becomes possible.

Though the number of reaction containers has been two in the present example, it is further acceptable to add a reaction container including another reagent.

According to the present example, more detailed information on the bacteria state may be obtained by reaction with individual reagents in one disposable chip, because a plurality of reagents may be added to a specimen.

EXAMPLE 3

An example using the measurement chip 30 for measurement of viable bacteria and killed bacteria in such a specimen including residual foods as suspensions of foods will be described.

Influence of residual foods on measurement results is made to the minimum by adding a process of removing the residual foods included in the specimen before mixing the specimen and the dyeing pigment. The specimen used here is obtained by stomaching of foods to be inspected after adding physiological salt solution with a mass ratio of ten to the foods.

Figure 16:
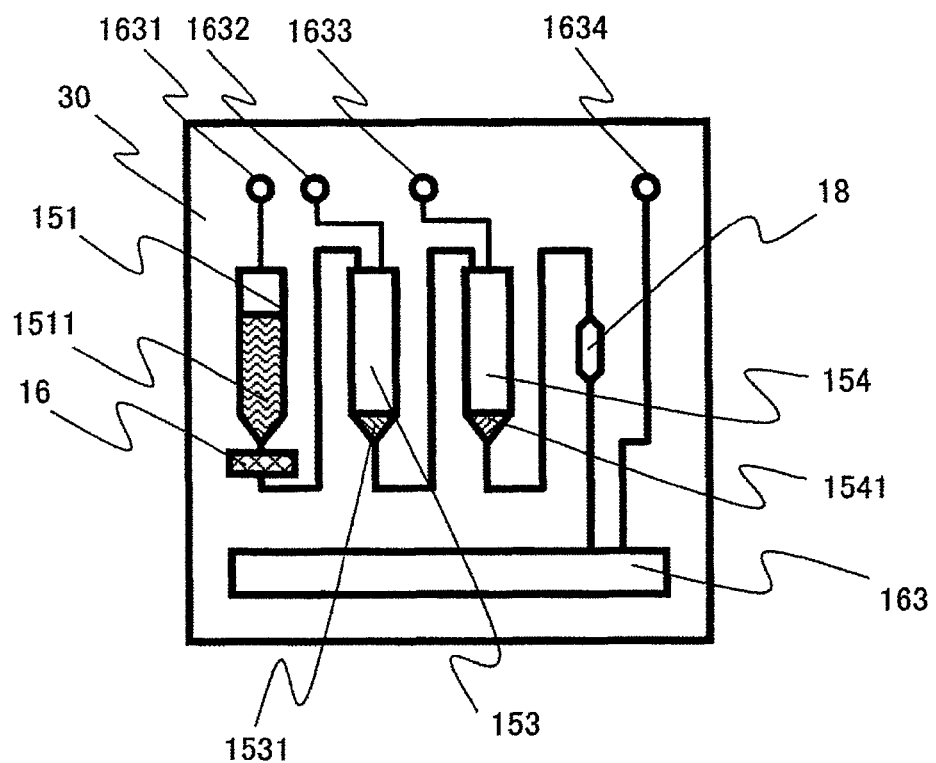
FIG. 16 is a plan view of a measurement chip according to further another embodiment of the present invention.

FIG. 16 is a plan view of the measurement chip 30. In the measurement chip 30, a residual food removing portion 16 is added to the measurement chip 20 (FIG. 15). The specimen container 1511, the residual food removing portion 16, the killed bacteria reagent holding container 153, the viable-and-killed bacteria dyeing reagent holding container 154, the specimen detection portion 18, and the detection liquid waste container 163 are connected in series through the solution flow path 157. When the specimen 1511 flows to the killed bacteria reagent holding container 153 through the residual food removing portion 16, the residual foods in the specimen 1511 are removed from the specimen 1511 by the residual food removing portion 16. After mixing with the killed bacteria dyeing reagent 1531, the number of viable bacteria and that of killed bacteria in the specimen 1511 are measured through the processes similar to those of the example 2.

Figure 17:
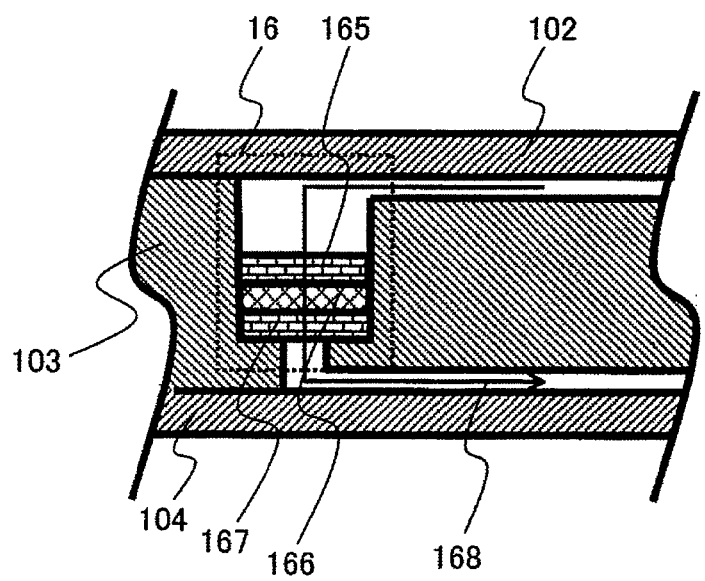
FIG. 17 is a cross sectional view of a residual food removing portion in a measurement chip according to another embodiment.

FIG. 17 is a cross sectional view of the measurement chip 30, showing the structure of the residual food removing portion 16.

The residual food removing portion 16 is formed in the through hole of the intermediate member 103, and includes an upper holding filter 165, a residual food capturing filter 166, and a lower holding filter 167. The residual food capturing filter 166 for capturing residual foods uses a depth filter, such as a glass filter, for removing a substance with a particle size of 10 μm through 100 μm or more, and the upper holding filter 165 and the lower holding filter 167, both of which hold the residual food capturing filter 166, use a porous member.

The specimen 1511 flows along the arrow 168, and residual foods (the particle sizes are 10 μm through 100 μm or more) larger than bacteria included in the specimen 1511 are captured by the residual food capturing filter 166.

According to the present example, the work load of a tester, and a risk that a tester is exposed to a bacteria and a dyeing reagent are reduced, because removal of residual foods in the specimen, dyeing of bacteria, and measurement of the number of cells may be continuously performed. Moreover, stable measurement results may be obtained because influence on measurement results by the skill of a tester may be made small.

EXAMPLE 4

There will be described an example in which a measurement chip is used for measurement of viable bacteria and killed bacteria in a specimen including residual foods smaller than bacteria such as pigments. The process for removing the residual foods includes a process for removing residual foods larger than bacteria, and a process for removing residual foods, such as pigments, smaller than bacteria. The specimen used here is obtained by stomaching of foods to be inspected after adding physiological salt solution with a mass ratio of ten to the foods to be inspected.

Figure 18:
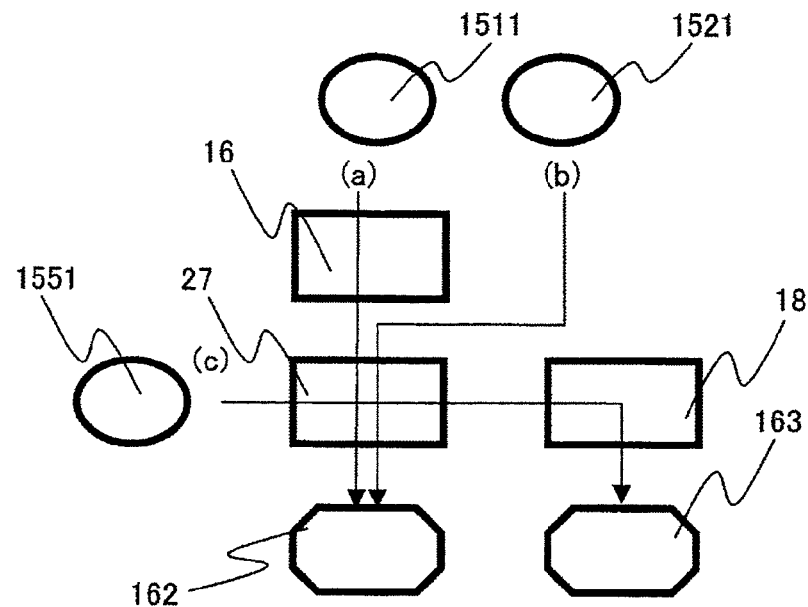
FIG. 18 is a process drawing for a microorganism testing device according to another embodiment.

FIG. 18 is a process drawing for processes in the measurement chip for measurement of bacteria. The measurement chip is provided with: a residual food removing portion for removing residuals larger than bacteria from a specimen 1511; a bacteria capturing portion 27 for capturing bacteria in the specimen 1511; and a bacteria detection portion 18 for detecting bacteria. A symbol (a) in the drawing indicates a processing path of the specimen 1511, a symbol (b) in the drawing indicates a processing path of the dyeing reagent 1521, and a symbol (c) in the drawing indicates a processing path of the bacteria eluent 1551. Processes for measurement of bacteria will be explained.

1. Process of removing residual foods is performed, following a processing path shown by (a). The specimen 1511 passes through a residual food removing portion 16 and the bacteria capturing portion 27. Residual foods, larger than bacteria, in the specimen 1511 are removed by the residual food removing portion 16, and bacteria in the specimen 1511 are captured by the bacteria capturing portion 27. Residual foods smaller than bacteria like a pigment, together with the specimen 1511, pass through the bacteria capturing portion, and enter a filtrate waste container 162 for removal.

2. Dyeing process of bacteria is performed, following a processing path shown by (b). The dyeing reagent 1521 for dyeing bacteria passes through the bacteria capturing portion 27, and dyes bacteria captured by the bacteria capturing portion 27. The surplus dyeing reagent 1521 enters the filtrate waste container 162 for removal.

3. The measurement process of bacteria dyed with a fluorochrome is performed, following a processing path shown by (c). The eluent 1551 for eluting bacteria captured by the bacteria capturing portion 27 passes through the bacteria capturing portion 27, elutes bacteria, and enters the bacteria detection portion 18. Microbial cells in the eluent 1551 are measured in the bacteria detection portion 18. After completion of measurement in the bacteria detection portion 18, the eluent 1551 enters a detection liquid waste container.

Figure 19:
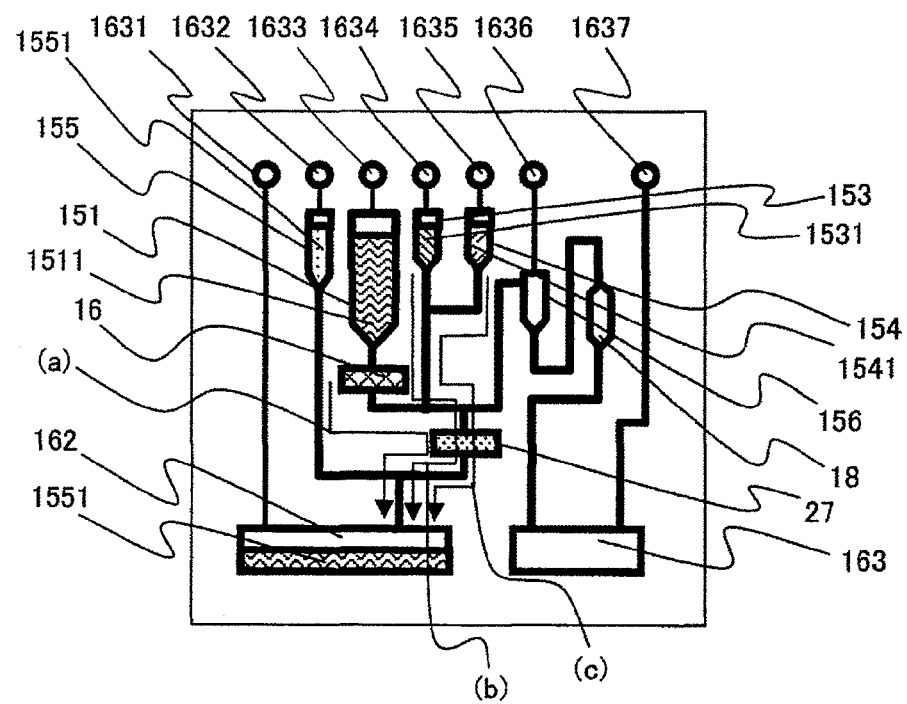
FIG. 19 is a plan view of a measurement chip according to further another embodiment to the present invention.

FIG. 19 is a plan view of a measurement chip 40. In the residual food removal process and in the dyeing process of bacteria, an arrow (a) in the drawing indicates a flowing direction of the specimen 1511, an arrow (b) in the drawing indicates a flowing direction of the killed bacteria dyeing reagent 1531, and an arrow (c) in the drawing indicates a flowing direction of the viable bacteria dyeing reagent 1541.

The measurement chip 40 includes: a specimen container 151 for holding the specimen 1511; a killed bacteria reagent holding container 153 for holding the killed bacteria dyeing reagent 1531 which dyes killed bacteria; a viable-and-killed bacteria dyeing reagent holding container 154 for holding the viable-and-killed bacteria dyeing reagent 1541 which dyes killed bacteria and viable bacteria; an eluent holding container 155 for holding eluent 1551; the residual food removing portion 16; the bacteria capturing portion 27; the bacteria detection portion 18; a filtrate waste container 162 which the specimen 1511 passing through the residual food removing portion 16 and the bacteria capturing portion 27 enters; a detection liquid container 156 which the eluent 1551 passing through the bacteria capturing portion 27 enters; a detection liquid waste container 163 which the eluent 1551 passing through the detection portion 18 enters; a solution flow path 157 which connects containers and processing portions, and in which the specimen 1511 and various kinds of reagents flow; ventilation ports 1631 through 1637 by which the specimens 1511 and the reagents in each of containers flow by air pressure; and an air flow path 158 through which the ventilation ports 1631 through 1637 and their respective containers are connected to each other.

The killed bacteria dyeing reagent 1531, the viable bacteria dyeing reagent 1541, and the eluent 1551 are encapsulated in the measurement chip 10 beforehand. For example, a PI (prosium iodide) is used as the killed bacteria dyeing reagent 1531, and, for example, a DAPI is used as the viable-and-killed bacteria dyeing reagent 1541.

The specimen 1511 is injected into the specimen container 151 through a ventilation port 1633 before inspection. Liquid foods are directly injected into an inspection chip 40, and solid foods are injected into the inspection chip 40 after the solid foods are made into suspension by stomaching of the foods.

The process of residual food removal is executed as follows.

Pressure from the delivery device 14 is applied to the specimen container 151 through the ventilation port 1633 to increase the air pressure therein. At the same time, the filtrate waste container 162 is opened to the air through the ventilation port 1631. Other ventilation ports 1632, and 1634 through 1637 are closed. By the difference in air pressure, the specimen 1511 flows to the filtrate waste container 162 along the arrow (a) through the residual food removing portion 16, and the bacteria capturing portion 27.

Residual foods, larger than bacteria, in the specimen 1551 are removed when the specimen 1551 passes through the residual food removing portion 16. Moreover, a bacteria in the specimen 1511 is captured by the bacteria capturing portion 27 when the bacteria passes through the bacteria capturing portion 27. As residual foods smaller than bacteria like a pigment, together with the specimen 1511, pass through the bacteria capturing portion, and enter a filtrate waste container 162, the residual foods may be removed from bacteria.

The dyeing process of bacteria following the removal process of residual foods is executed as shown in the following.

Pressure from the delivery device 14 is applied to the killed bacteria reagent holding container 153 through the ventilation port 1634. At the same time, the filtrate waste container 162 is opened to the air through the ventilation port 1631. Other ventilation ports 1632, 1633, and 1635 through 1637 are closed. By the difference in air pressure, the killed bacteria dyeing reagent 1531 flows from the killed bacteria reagent holding container 153 to the filtrate waste container 162 through the bacteria capturing portion 27 along the arrow (b). When the killed bacteria dyeing reagent 1531 passes through the bacteria capturing portion 27, the captured killed bacteria are dyed.

Subsequently, pressure from the delivery device 14 is applied to the viable-and-killed bacteria dyeing reagent holding container 154 through a ventilation port 1635 to increase the pressure in the container 154. At the same time, the filtrate waste container 162 is opened to the air through the ventilation port 1631. Other ventilation ports 1632 through 1634, 1636, and 1637 are closed. By the difference in air pressure, the viable-and-killed bacteria dyeing reagent 1541 flows from the viable-and-killed bacteria dyeing reagent holding container 154 to the filtrate waste container 162 through the bacteria capturing portion 27 along the arrow (c). When the viable-and-killed bacteria dyeing reagent 1541 passes through the bacteria capturing portion 27, all captured bacteria are dyed.

By opening the filtrate waste container 162 to the air, and letting air in the measurement chip 40 escape to the outside, the specimen 1511, the killed bacteria reagent holding container 153, and the viable-and-killed bacteria dyeing reagent holding container 154 may be prevented from flowing into the bacteria detection portion 18.

Figure 20:
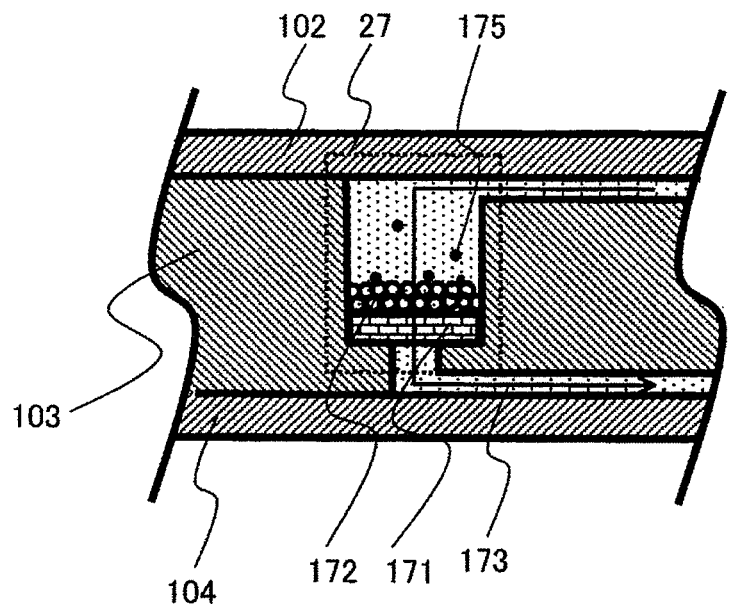
FIG. 20 is a cross sectional view of a bacteria capturing portion in FIG. 19.

FIG. 20 is a cross sectional view of the measurement chip 10, showing the structure of the bacteria capturing portion 27.

The bacteria capturing portion 27 is located in the through hole in the intermediate member 103, and includes a bacteria holding fine particle 172 and a fine particle holding filter 171. The bacteria holding fine particle 172 is a particle within a diameter of 0.1 µm through 100 µm, and the fine particle holding filter 171 is provided for holding the bacteria holding particle 172 in such a way that the fine particle 172 is not flown.

In the residual food removal process, the bacteria 175 in the specimen 1511 may not pass through interspaces formed by the bacteria holding particles 172 when the specimen 1511 passes through the bacteria capturing portion 27, because the diameter of the bacteria 175 is about 1 µm. However, residual foods such as pigments smaller than bacteria may be removed from the bacteria 175 because the residual foods such as pigments smaller than bacteria pass along the arrow 173. Even in the subsequent dyeing process of the bacteria, surplus dyeing pigments which does not dye bacteria may be removed from the bacteria 175 because the surplus dyeing pigments pass through the bacteria capturing portion 27.

Figure 21:
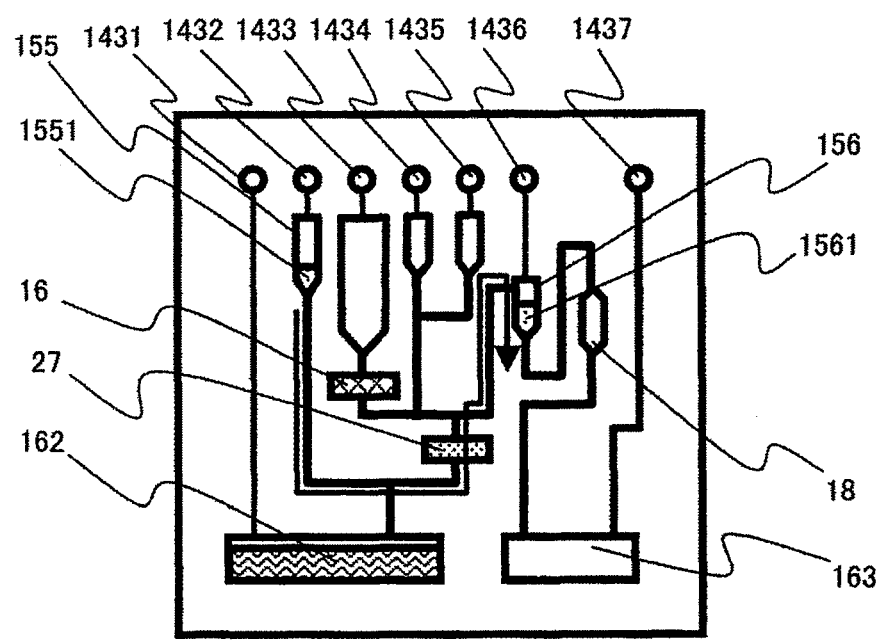
FIG. 21 is a plan view of a measurement chip according to further another embodiment of the present invention.

FIG. 21 is a view showing a flowing state of the eluent 1551 in the measurement chip 40. Pressure from the delivery device 14 is applied to the eluent holding container 155 through the ventilation port 1632 to increase the pressure therein. At the same time, the detection liquid container 156 and the detection liquid waste container 163 are opened to the air through the ventilation ports 1636 and 1637. Other ventilation ports 1631, and 1633 through 1635 are closed. The eluent 1551 flows from the eluent holding container 155 to the detection liquid container 156 through the bacteria capturing portion 27 by the difference in the air pressure. When the eluent 1551 flows through the bacteria capturing portion 27, the captured bacteria is eluted.

The eluent 1551 does not flow out to the bacteria detection portion 18, because the highest point of the flow path connecting the detection liquid container 156 and the bacteria detection portion 18 is higher than the water level of the eluent 1551 flowing into the detection liquid container 156, and the air in the reaction container is discharged along the arrow 1762 to the outside through the ventilation port 1632. The bacteria may be also concentrated by making the liquid volume of the eluent 1551 smaller than that of the specimen 1511.

Air bubbles is removed by holding the eluent 1551 in the detection liquid container 156 once, wherein the air bubbles are mixed into the eluent 1551 when the eluent 1551 passes through the bacteria capturing portion 27. Preferably, the air bubbles are removed as much as possible because there is a possibility that detection is blocked in the subsequent detection process of bacteria.

Subsequently, the eluent 1551 flows to the detection liquid waste container 163 through the bacteria detection portion 18 in the bacteria detection process. Bacteria in the eluent 1551 are measured in the bacteria detection portion 18.

Figure 22:
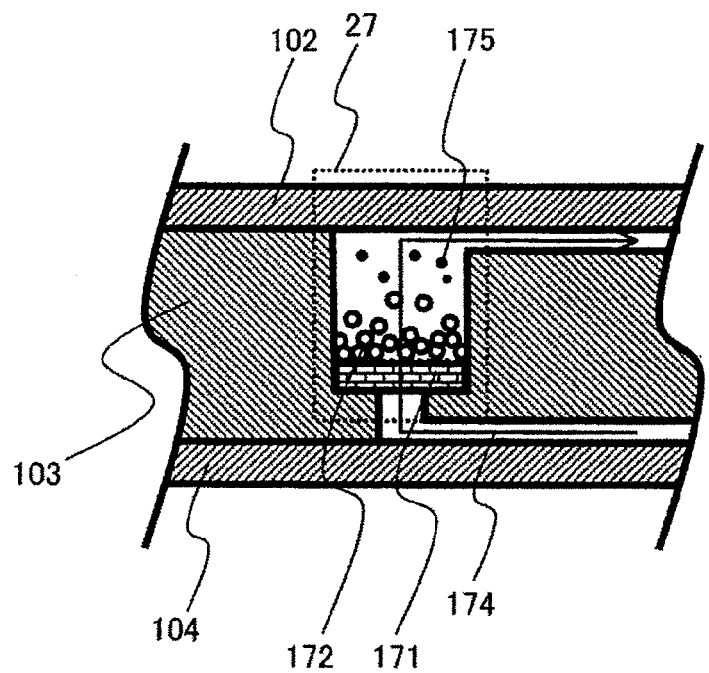
FIG. 22 is a cross sectional view of a bacteria capturing portion in FIG. 21.

FIG. 22 is a view explaining a principle that the eluent 1551 passes through the bacteria capturing portion 27, and captured bacteria are eluted. The eluent 1551 flows to the bacteria capturing portion 27 along the arrow 174. As the bacteria holding particle 172 is moved in the flow direction by the flow of the arrow 174, the bacteria 175 held in the interspaces formed by the bacteria holding particles 172 flows with the flow of eluent 1551, and is eluted in the bacteria capturing portion 27.

According to the present example, removal of residual foods, dyeing of bacteria, and measurement of the number of cells may be continuously performed even in a specimen including residual foods smaller than bacteria such as pigments. As the work load of a tester, and a risk that a tester is exposed to a bacteria and a dyeing reagent may be reduced, and the influence of tester skill on measurement results may be made small to obtain stable measurement results.

EXAMPLE 5

There will be described an example in which one measurement chip 50 is used for measurement of bacteria in two kinds of specimens.

Figure 23:
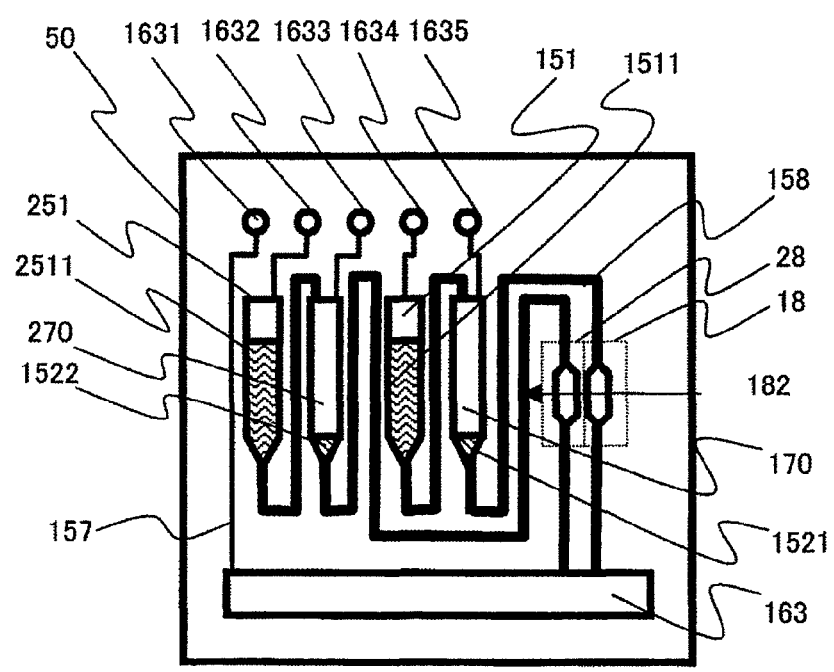
FIG. 23 is a plan view of a measurement chip according to further another embodiment of the present invention.

FIG. 23 is a plan view of a measurement chip 50. The measurement chip 50 has a structure in which two flow path structures of the measurement chip 10 (FIG. 5) are arranged in parallel.

The measurement chip 50 includes: specimen containers 151 and 251 for holding specimens 1511 and 1512; a reaction container 170 for mixing the specimen 1511 and a dyeing reagent 1521 for reaction; a reaction container 270 for mixing the specimen 1512 and a dyeing reagent 1522 for reaction; bacteria detection portions 18 and 28; and a detection liquid waste container 163 into which both liquid mixture of the specimen 1511 and the dyeing reagent 1521, has passed through the bacteria detection portions 18, and liquid mixture of the specimen 1521 and the dyeing reagent 1522, has passed through the bacteria detection portions 28, enter.

The specimen container 151, the reaction container 170, the bacteria detection portion 18, and the detection liquid waste container 163 are connected to each other through solution flow path 157, and the specimen container 251, the reaction container 270, the bacteria detection portion 28, and the detection liquid waste container 163 are connected through the solution flow path 157. The ventilation ports 1631 through 1633 are connected to their respective containers through the air flow path 158. The design has been made in such a way that the depth and width of the solution flow path 157 are within a range of 10 μm through 1 mm, the depth and width of the air flow path 158 are within a range of 10 μm through 1 mm, and the sectional area of the solution flow path 157 is larger than that of the air flow path 158.

The dyeing reagents 1521 and 1522 are encapsulated in the reaction container 170, and 270 beforehand. Accordingly, deterioration effects by external environment, and a possibility that a tester is exposed to various kinds of reagents are suppressed to the minimum. The specimens 1511, and 1512 are injected into the specimen containers 151, and 251 through the ventilation ports 1632 and 1634 before inspection.

After the specimens 1511, and 1521 are injected into the specimen containers 151, and 251, measurements are performed. In the same manner as that of the example 1, the specimen 1511 flows to the reaction container 170, and, after the specimen 1511 is mixed with the dyeing reagent 1521, the liquid mixture of two liquids passes through the bacteria detection portion 18, and flows into the detection liquid waste container 163. Bacteria in the liquid mixture are detected in the bacteria detection portion 18. Similarly, the specimen 2511 also flows to the reaction container 270, and, after being mixed with the dyeing reagent 1522, the liquid mixture of two liquids pass through the bacteria detection portion 28, and flows to the detection liquid waste container 163. Bacteria in the liquid mixture are detected in the bacteria detection portion 28.

Figure 24:
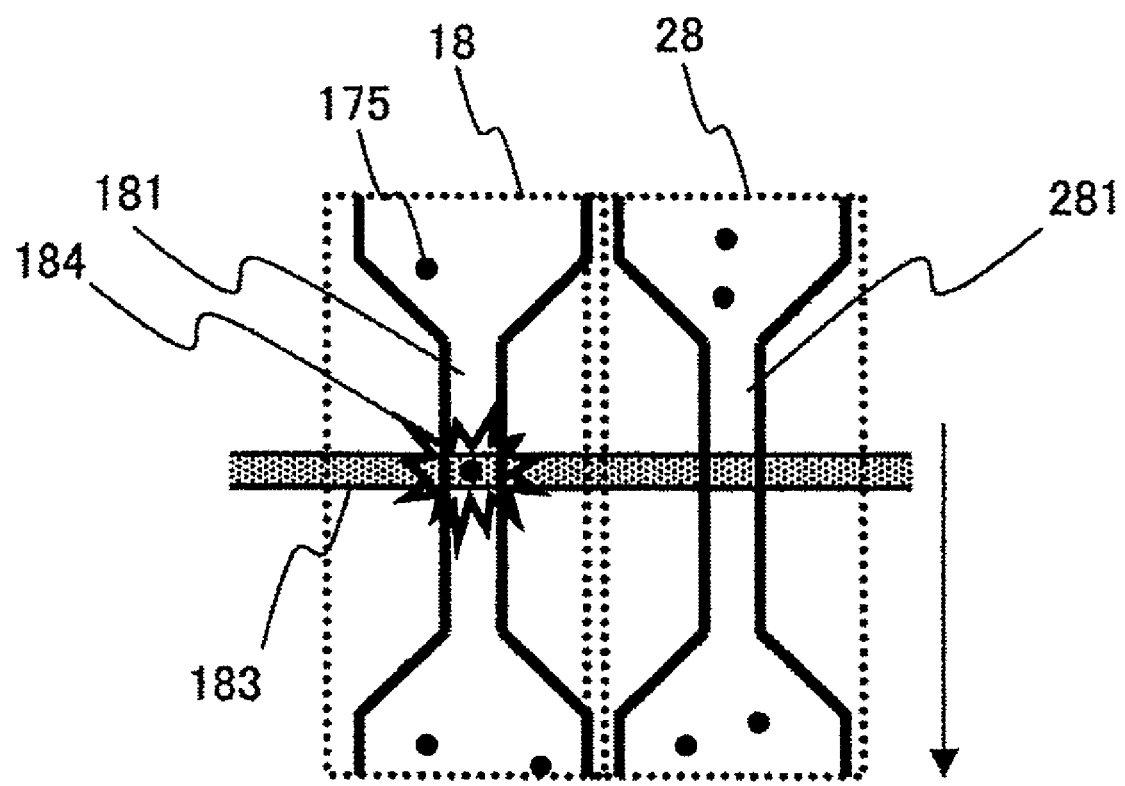
FIG. 24 is an enlarged plan view of the bacteria detection portion shown in FIG. 23.

FIG. 24 is an enlarged plan view of the bacteria detection portions 18 and 28. The design has been made in such a way that, with regard to the detection flow path 181 in the bacteria detection portions 18, and a detection flow path 281 in the bacteria detection portion 28, both the flow path widths and depths are within a range of 0.1 μm through 0.1 mm, and the lengths are within a range of 10 μm through 10 mm and are designed to be longer than the width and depth of the flow path. Furthermore, the sectional areas of the detection flow paths 181, and 281 are designed to be smaller than that of the solution flow path 157. The positions of the detection flow paths 181 and 281 are in parallel to each other. The excitation light 183 for detection of bacteria from the detection device 12 (FIG. 2) enters in such a way that the light 183 crosses the detection flow paths 181 and 281. The dyed bacteria 175 emits fluorescence 184 when the cell 175 passes through the excitation light 183. The fluorescence 184 is detected by the detection device 12.

Figure 25:
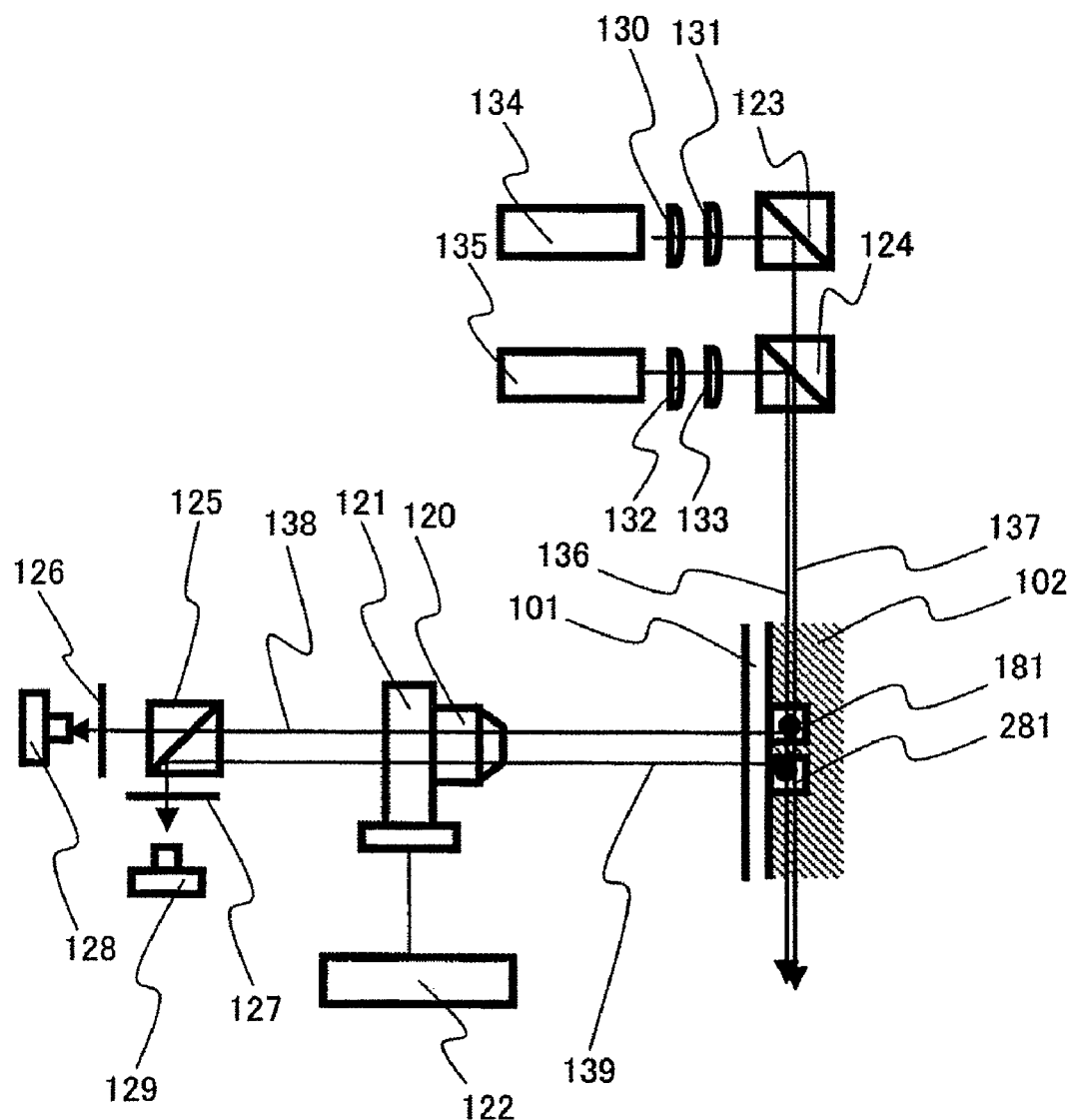
FIG. 25 is a configuration diagram of a detection device in a microorganism testing device according to one embodiment.

FIG. 25 is a configuration diagram of the optical system of the detection device 12. Though optical components used are similar to those in the Examples 1 through 4, an arrangement of optical components for the optical path from the excitation light source to the detection flow path in the optical system in the Examples 1 through 4 is required to be changed because the excitation light enters in such a way that the light crosses the detection flow paths 181 and 281. Moreover, as the excitation light passes through the upper member 102 in the measurement chip 10, the upper member 102 includes optically transparent materials such as glass, quartz, polymethacrylate, and PDMS.

Here, an optical system suitable for use of two kinds of dyeing pigments, that is, ethidium bromide (the excitation wavelength: 520 nm, and the fluorescent wavelength: 615 nm) and DAPI (the excitation wavelength: 360 nm, and the fluorescent wavelength: 460 nm), will be explained.

The excitation light 136 (wavelength 360 nm) output from the short wave laser 134 is condensed into an elliptical shape by the cylindrical lenses 130 and 133, is reflected on the short wavelength dichroic mirror 123, passes through the medium-wavelength dichroic mirror 124, and the upper member 102, and excites DAPI dyeing the bacteria 175 flowing in the detection flow paths 181 and 281. Fluorescence 138 (wavelength 460 nm) from the DAPI passes through the long-wavelength dichroic mirror 125 and the short wavelength optical filter 126, and enters the short wavelength photomultiplier 128. The fluorescence 138 detected by the short wavelength photomultiplier 128 is converted into an electric signal, and the electric signal is sent to the system device 11.

On the other hand, excitation light 137 (wavelength 530 nm) output from the long wavelength laser 135 is condensed into an elliptical shape by the cylindrical lenses 132 and 133, is reflected on the medium-wavelength dichroic mirror 124, and excites ethidium bromide which has dyed the bacteria 175 which flows in the detection flow paths 181 and 281. Fluorescence 139 (wavelength 620 nm) from the ethidium bromide is reflected on the long-wavelength dichroic mirror 125, passes through the long wavelength optical filter 127, and enters the long wavelength photomultiplier 129. The fluorescence 138 detected by the long wavelength photomultiplier 129 is converted into an electric signal, and the electric signal is sent to the system device 11. The system device 11 processes the electric signals sent from the short wavelength photomultiplier 128 and the long wavelength photomultiplier 129, and outputs information on the number of bacteria as an inspection result to the output device 111.

Distinction between the fluorescence signal from the bacteria flowing in the detection flow path 181 and the fluorescence signal from the bacteria flowing in the detection flow path 182 is based on any one of the following methods:

1. The distinction is made from fluorescence spectra, using different dyeing reagents;

The numbers of bacteria may be measured at the same time even when specimens have a large number of bacteria, because distinction by a fluorescent spectrum may be made even when bacteria flowing in the detection flow path 181, and bacteria flowing in the detection flow path 281 cross the excitation light at the same time.

2. The number of bacteria is sequentially measured for each specimen.

Though total measuring time is increased corresponding to the number of specimens, the number of dyeing reagents is not required to be increased for distinction.

3. The flow velocity is changed for each of detection flow paths, and the distinction is made based on the pulse widths of fluorescence. The number of dyeing reagents is not increased for distinction, and the numbers of bacteria may be measured at the same time.

Though, in the present examples, the numbers of bacteria in two kinds of specimens have been measured in a state in which two flow path structures of the measurement chip 10 (FIG. 4) are arranged in one measurement chip 50 in parallel, measurement of the numbers of bacteria may be made for a plurality of specimens by further parallel arrangement of the flow path structures.

According to the present example, the number of measurement chips consumed may be controlled even when there are a large number of specimens, because measurement of the numbers of bacteria may be performed for a plurality of specimens by use of one measurement chip.

As described above, holding the liquid mixture of a specimen and a material in a reaction container, and flowing of liquid mixture of a specimen and a material from a reaction container to a detection flow path may be controlled by switching of the state of the reaction container between a sealed state and a state open to the atmospheric pressure. Accordingly, dyeing of bacteria and particle measurement by the flow cytometry method may be performed in one chip.

Moreover, when a method for removing materials other than a target particle is provided in a chip, processes from pretreatment of residual food removal and bacteria dyeing to the bacteria measurement by the flow cytometry method may be performed in one chip. Accordingly, quick bacteria measurement may be performed for various types of food specimens.

What is claimed is:

1. A microorganism testing device for measuring a microorganism included in food, said microorganism testing device comprising a measurement chip for holding a specimen including bacteria and a dyeing reagent in said chip, a holder for holding said measurement chip, and a delivery device for delivering said specimen and said dyeing reagent through a chip connecting tube connected to said measurement chip, which testing device irradiates a specimen in said measurement chip with excitation light to detect said bacteria as an electric signal, wherein said measurement chip is held in a standing state by said holder, and wherein said measurement chip includes:

a specimen container for holding said specimen;

a reaction container for mixing said specimen and a dyeing reagent for reaction into a liquid mixture;

a bacteria detection portion including a flow path being irradiated with said excitation light;

a detection liquid waste container into which said liquid mixture which has passed said bacteria detection portion enters;

a solution flow path which connects said specimen container, said reaction container, and said bacteria detection portion, and in which said specimen and said liquid mixture flow; and a ventilation port which is connected to said specimen container, said reaction container, and said detection liquid waste container through a air flow path and is connected to said chip connecting tube, wherein the highest point of said solution flow path connecting said specimen container and said reaction container is configured to be higher than a water level of the specimen in said specimen container, wherein the highest point of said solution flow path connecting said reaction container and said bacteria detection portion is configured to be higher than a water level of the liquid mixture in said reaction container, and wherein said microorganism testing device is configured such that a portion of the specimen is flowed continuously through said bacteria detection portion so that bacteria in said specimen are detected in said bacteria detection portion by applying pressure to said specimen container, said reaction container, and said detection liquid waste container from said delivery device through said ventilation port, by switching of the states of said specimen container, said reaction container, and said detection liquid waste container between a sealed state and a state open to the atmospheric pressure, by moving said specimen to said reaction container to mix said specimen and said dyeing reagent in said reaction container, and by moving of said liquid mixture to said detection liquid waste container through said bacteria detection portion.

2. The microorganism testing device as claimed in claim 1, wherein said microorganism testing device is configured such that air flows into said reaction container through said solution flow path which is disposed downstream of said reaction container so that the liquid mixture in said reaction container is stirred for promoting mixing of the liquid mixture.

3. The microorganism testing device as claimed in claim 1, wherein said flow path in the bacteria detection portion is designed in such a way that the flow path width and depth are 0.1 μm through 0.1 mm, and the length is within a range of 10 μm through 10 mm.

4. A microorganism testing device for measuring a microorganism included in a food, said microorganism testing device comprising a measurement chip for holding a specimen including bacteria and a plurality of dyeing reagents in said chip, a holder for holding said measurement chip, and a delivery device for delivering said specimen and said dyeing reagents through a chip connecting tube connected to said measurement chip, which testing device irradiates a specimen in said measurement chip with excitation light to detect said bacteria as an electric signal, wherein said measurement chip is held in a standing state by said holder, wherein said measurement chip includes:

a specimen container for holding said specimen;

a first dyeing reagent holding container which contains a first dyeing reagent therein, and which mixes said specimen and said first dyeing reagent for reaction into a first liquid mixture;

a second dyeing reagent holding container which contains a second dyeing reagent therein, and which mixes said second dyeing reagent and said first liquid mixture for reaction into a second liquid mixture;

a bacteria detection portion including a flow path being irradiated with said excitation light;

a detection liquid waste container into which said second liquid mixture which has passed said bacteria detection portion enters;

a solution flow path which connects said specimen container, said first dyeing reagent holding container, said second dyeing reagent holding container and said bacteria detection portion, and in which said specimen, said first liquid mixture, and said second liquid mixture flow; and a ventilation port which is connected to said specimen container, said first dyeing reagent holding container, said second dyeing reagent holding container, and said detection liquid waste container through an air flow path and is connected to said chip connecting tube, wherein the highest point of said solution flow path connecting said first dyeing reagent holding container and said second dyeing reagent holding container is designed to be higher than a water level of said first liquid mixture in said first dyeing reagent holding container; and wherein said microorganism testing device is configured such that bacteria in said specimen are detected in said bacteria detection portion by applying pressure to said specimen container, said first dyeing reagent holding container, said second dyeing reagent holding container, and said detection liquid waste container from said delivery device through said ventilation port, by switching of the states of said specimen container, said first dyeing reagent holding container, said second dyeing reagent holding container, and said detection liquid waste container between a sealed state and a state open to the atmosphere pressure, by moving said specimen to said first dyeing reagent holding container to mix said specimen and said first dyeing reagent in said first dyeing reagent holding container, by moving said first liquid mixture to said second dyeing reagent holding container to mix said first liquid mixture and said second dyeing reagent, and by moving of said second liquid mixture in said second dyeing reagent holding container to said detection liquid waste container through said bacteria detection portion.

5. A measurement chip included in microorganism testing device for measuring a microorganism included in a food, wherein a specimen mixed with a dyeing reagent is included in said measurement chip, and said specimen is irradiated with excitation light to detect bacteria as an electric signal, wherein said measurement chip is held in a standing state by a holder of said microorganism testing device, wherein said measurement chip includes:

a specimen container into which said specimen is injected;

a dyeing reagent holding container which contains said dyeing reagent therein beforehand, and which mixes said dyeing reagent and said specimen for reaction into a liquid mixture;

a first solution flow path which connects said specimen container and said dyeing reagent holding container, and in which said specimen flows, wherein the highest point of said first solution flow path is designed to be higher than a water level of said specimen in said specimen container;

a bacteria detection portion including a flow path being irradiated with said excitation light;

a second solution flow path which connects said dyeing reagent holding container and said bacteria detection portion, and in which said liquid mixture flows, wherein the highest point of said second solution flow path is designed to be higher than a waste level of said liquid mixture in said dyeing reagent holding container;

a detection liquid waste container into which said liquid mixture which has passed said bacteria detection portion enters;

a plurality of air flow paths which are connected with said specimen container, said dyeing reagent holding container, and said detection liquid waste container, respectively; and a plurality of ventilation ports including a first port for the air flow path connected with said specimen container, a second port for the air flow path connected with said dyeing reagent holding container, and a third port for the air flow path connected with said detection liquid waste container, wherein said plurality of ventilation ports are connected with a delivery device of said microorganism testing device, and the delivery device applies to pressure through said ventilation ports and switches the states of said specimen container, said dyeing reagent holding container, and said detection liquid waste container to a state open to the atmospheric pressure, and wherein the application of the pressure through said ventilation ports allows to move said specimen in said specimen container to said dyeing reagent holding container, and to move said liquid mixture in said dyeing reagent holding container to said bacteria detection portion.

6. A measurement chip included in a microorganism testing device for measuring a microorganism included in a food, wherein a specimen mixed with dyeing reagents is included in said measurement chip, and the specimen is irradiated with excitation light to detect bacteria as an electric signal, wherein said measurement chip is held in a standing state by a holder of said microorganism testing device, wherein said measurement chip includes:

a specimen container into which said specimen is injected;

a plurality of dyeing reagent holding containers including a first dyeing reagent holding container and a second dyeing reagent holding container, wherein each dyeing reagent holding container contains said dyeing reagent therein beforehand, wherein said first dying reagent holding container mixes said dyeing reagent and said specimen for reaction into a first liquid mixture, and wherein said second dyeing reagent holding container mixes said first liquid mixture and said dyeing reagent for reaction into a second liquid mixture;

a first solution flow path which connects said specimen container and said first dyeing reagent holding container, and in which said specimen flows, wherein the highest point of said first solution flow path is designed to be higher than a water level of said specimen in said specimen container;

a second solution flow path which connects said first dyeing reagent holding container and said second dyeing reagent holding container, and in which said first liquid mixture flows, wherein the highest point of said second solution flow path is designed to be higher than a water level of said first liquid mixture in said first dyeing reagent holding container;

a bacteria detection portion including a flow path being irradiated with said excitation light;

a third solution flow path which connects said second dyeing reagent holding container and said bacteria detection portion, and in which said second liquid mixture flows, wherein the highest point of said third solution flow path is designed to be higher than a water level of said second liquid mixture in said second dyeing reagent holding container;

a detection liquid waste container into which said second liquid mixture which has passed said bacteria detection portions enters;

a plurality of air flow paths which are connected with said specimen container, said first dyeing reagent holding container, said second dyeing reagent holding container, and said detection liquid waste container, respectively; and a plurality of ventilation ports including a first port for the air flow path connected with said specimen container, a second port for the air flow path connected with said first dyeing reagent holding container, a third port for the air flow path connected with the second dyeing reagent holding container, and a fourth port for the air flow path connected with said detection liquid waste container, wherein said plurality of ventilation ports are connected with a delivery device of said microorganism testing device, and the delivery device applies pressure through said ventilation ports and switches the tastes of said specimen container, said first dyeing reagent holding container, said second dyeing reagent holding container, and said detection liquid waste container to state open to the atmospheric pressure, and wherein the application of the pressure through said ventilation ports allows to move said specimen in said specimen container to said first dyeing reagent holding container, to move said first liquid mixture in said first dyeing reagent holding container to said second dyeing reagent holding container, and to move said second liquid mixture in said second dyeing reagent holding container to said bacteria detection portion.

7. The microorganism testing device as claimed in claim 1, comprising:

a reagent container including a dyeing reagent, wherein said specimen in said specimen container and said dyeing reagent flow into said reaction container.

8. The microorganism testing device as claimed in claim 1, comprising:

a plurality of said reaction containers, wherein one of said reaction containers is used as a killed bacteria dyeing reagent holding container for holding a killed bacteria dyeing pigment, and other containers are used as a viable-and-killed bacteria dyeing reagent holding container for holding viable-and-killed bacteria dyeing pigment.

9. The microorganism testing device as claimed in claim 1, comprising:

a residual food removing portion which is located between said specimen container and said reaction container, and removes residual foods.

10. The microorganism testing device as claimed in claim 1, comprising:

an eluent holding container for holding eluent;

a bacteria capturing portion into which said liquid mixture flows; and a filtrate waste container into which a specimen has passed through said bacteria capturing portion enters.

11. The microorganism testing device as claimed in claim 1, comprising:

a plural set of said specimen containers and said reaction containers, wherein said liquid mixture in each of said reaction containers flows into said bacteria detection portion.

12. The microorganism testing device as claimed in claim 1, comprising:

temperature control means for controlling the temperature of said measurement chip.

13. The microorganism testing device as claimed in claim 1, wherein said bacteria detection portion includes a flow path, a part or the whole of which is formed of an optically transparent material.

* * * * *